United States Patent
Nolan et al.

(10) Patent No.: US 10,039,816 B2
(45) Date of Patent: Aug. 7, 2018

(54) SIDEROPHORE-BASED IMMUNIZATION AGAINST GRAM-NEGATIVE BACTERIA

(71) Applicants: Massachusetts Institute of Technology, Cambridge, MA (US); The Regents of the University of California, Oakland, CA (US)

(72) Inventors: Elizabeth Marie Nolan, Cambridge, MA (US); Phoom Chairatana, Cambridge, MA (US); Manuela Raffatellu, Irvine, CA (US); Martina Sassone Corsi, Irvine, CA (US); Araceli Perez-Lopez, Irvine, CA (US)

(73) Assignees: Massachusetts Institute of Technology, Cambridge, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/700,397

(22) Filed: Apr. 30, 2015

(65) Prior Publication Data

US 2016/0022794 A1    Jan. 28, 2016

Related U.S. Application Data

(60) Provisional application No. 61/986,200, filed on Apr. 30, 2014.

(51) Int. Cl.
*A61K 39/12* (2006.01)
*G01N 33/00* (2006.01)
(Continued)

(52) U.S. Cl.
CPC ........ *A61K 39/025* (2013.01); *A61K 39/0013* (2013.01); *A61K 47/646* (2017.08);
(Continued)

(58) Field of Classification Search
CPC ........ A61K 39/12; C07K 14/11; C07K 14/16; C07K 19/00; G01N 33/00
See application file for complete search history.

(56) References Cited

U.S. PATENT DOCUMENTS

2009/0104220 A1* 4/2009 Bianchi ................ C07K 14/005
424/193.1

FOREIGN PATENT DOCUMENTS

WO    WO 2010/031675    * 10/2010 ............. A61K 31/42
WO    WO 2010/123845 A2    10/2010

OTHER PUBLICATIONS

Zheng et al., (J. Am. Chem Soc. 2012. 134(44):18388-18400).*
(Continued)

*Primary Examiner* — Jana A Hines
(74) *Attorney, Agent, or Firm* — Wolf, Greenfield & Sacks, P.C.

(57) ABSTRACT

The present invention provides novel enterobactin-carrier protein conjugates and salmochelin-carrier protein conjugates, such as compounds of Formula (I), and salts thereof. The present invention also provides compositions, kits, and methods that involve the compounds of Formula (I) and are useful in inducing an immune response, treating a bacterial infection and/or inflammatory bowel disease in a subject, preventing a bacterial infection and/or inflammatory bowel disease in a subject, or inhibiting the growth of or killing a bacterium.

13 Claims, 24 Drawing Sheets

Enterobactin (Ent)

Monoglucosylated Ent (MGE)

Diglucosylated Ent (DGE)
(Salmochelin S4)

Glu-DHB-Ser Monomer
Salmochelin SX

(51) Int. Cl.
  A61K 39/02    (2006.01)
  A61K 39/00    (2006.01)
  C07K 19/00    (2006.01)
  G01N 33/569   (2006.01)
  A61K 47/64    (2017.01)

(52) U.S. Cl.
  CPC .......... *A61K 47/6415* (2017.08); *C07K 19/00* (2013.01); *G01N 33/56916* (2013.01); *A61K 2039/6037* (2013.01); *A61K 2039/627* (2013.01); *G01N 2333/245* (2013.01); *G01N 2333/255* (2013.01); *G01N 2469/20* (2013.01)

(56) References Cited

OTHER PUBLICATIONS

Bäumler et al., IroN, a novel outer membrane siderophore receptor characteristic of *Salmonella enterica*. J Bacteriol. Mar. 1998;180(6):1446-53.

Crosa et al., Genetics and assembly line enzymology of siderophore biosynthesis in bacteria. Microbiol Mol Biol Rev. Jun. 2002;66(2):223-49.

Ecker et al., Substituted complexes of enterobactin and synthetic analogs as probes of the ferric-enterobactin receptor in *Escherichia coli*. J. Am. Chem. Soc. 1988; 110(8):2457-64.

Fischbach et al., in vitro characterization of IroB, a pathogen-associated C-glycosyltransferase. Proc Natl Acad Sci U S A. Jan. 18, 2005;102(3):571-6. Epub Dec. 14, 2004.

Ji et al., Iron transport-mediated drug delivery: practical syntheses and in vitro antibacterial studies of tris-catecholate sidero-phore-aminopenicillin conjugates reveals selectively potent anti-pseudomonal activity. J Am Chem Soc. Jun. 20, 2012;134(24):9898-901. doi: 10.1021/ja303446w. Epub Jun. 6, 2012.

Lagos et al., Structure, organization and characterization of the gene cluster involved in the production of microcin E492, a channel-forming bacteriocin. Mol Microbiol. Oct. 2001;42(1):229-43.

Lin et al., In vitro characterization of salmochelin and enterobactin trilactone hydrolases IroD, IroE, and Fes. J Am Chem Soc. Aug. 10, 2005;127(31):11075-84.

Loomis et al., Solution equilibria of enterobactin and metal-enterobactin complexes. Inorg. Chem. 1991;30(5):906-11.

Nolan et al., Biosynthetic tailoring of microcin E492m: post-translational modification affords an antibacterial siderophore-peptide conjugate. J Am Chem Soc. Nov. 21, 2007;129(46):14336-47. Epub Oct. 31, 2007.

Raymond et al., Enterobactin: an archetype for microbial iron transport. Proc Natl Acad Sci U S A. Apr. 1, 2003;100(7):3584-8. Epub Mar. 24, 2003.

Rodgers et al., Ferric ion sequestering agents. 15. Synthesis, solution chemistry, and electrochemistry of a new cationic analog of enterobactin. Inorg. Chem. 1987;26(10):1622-5.

Singh et al., HaptenDB: a comprehensive database of haptens, carrier proteins and anti-hapten antibodies. Bioinformatics. Jan. 15, 2006;22(2):253-5.

Stack et al., Rational reduction of the conformational space of a siderophore analog through nonbonded interactions: the role of entropy in enterobactin. J Am Chem Soc. 1993;115(14):6466-7.

Tor et al., Tripodal Peptides with Chiral Conformations Stabilized by Intersrands Hydrogen Bonds. J. Am. Chem. Soc. 1992;114(17):6653-61.

Bergeron et al., Vibriobactin antibodies: a vaccine strategy. J Med Chem. Jun. 25, 2009;52(12):3801-13. doi:10.1021/jm900119q.

Huang et al., Peg as a spacer arm markedly increases the immunogenicity of meningococcal group Y polysaccharide conjugate vaccine. J Control Release. Nov. 28, 2013;172(1):382-9. doi: 10.1016/j.jconrel.2013.03.008. Epub Mar. 17, 2013.

Mueller et al., Salmochelin, the long-overlooked catecholate siderophore of *Salmonella*. Biometals. Aug. 2009;22(4):691-5. doi:10.1007/s10534-009-9217-4. Epub Feb. 13, 2009.

Mike et al., Siderophore vaccine conjugates protect against uropathogenic *Escherichia coli* urinary tract infection. Proc Natl Acad Sci U S A. Nov. 22, 2016;113(47):13468-13473. doi: 10.1073/pnas.1606324113. Epub Nov. 7, 2016.

Sassone-Corsi et al., Siderophore-based immunization strategy to inhibit growth of enteric pathogens. Proc Natl Acad Sci U S A. Nov. 22, 2016;113(47):13462-13467. doi: 10.1073/pnas.1606290113. Epub Nov. 7, 2016.

PCT/US2015/028469, dated Jul. 28, 2015, Invitation to Pay Additional Fees.

* cited by examiner

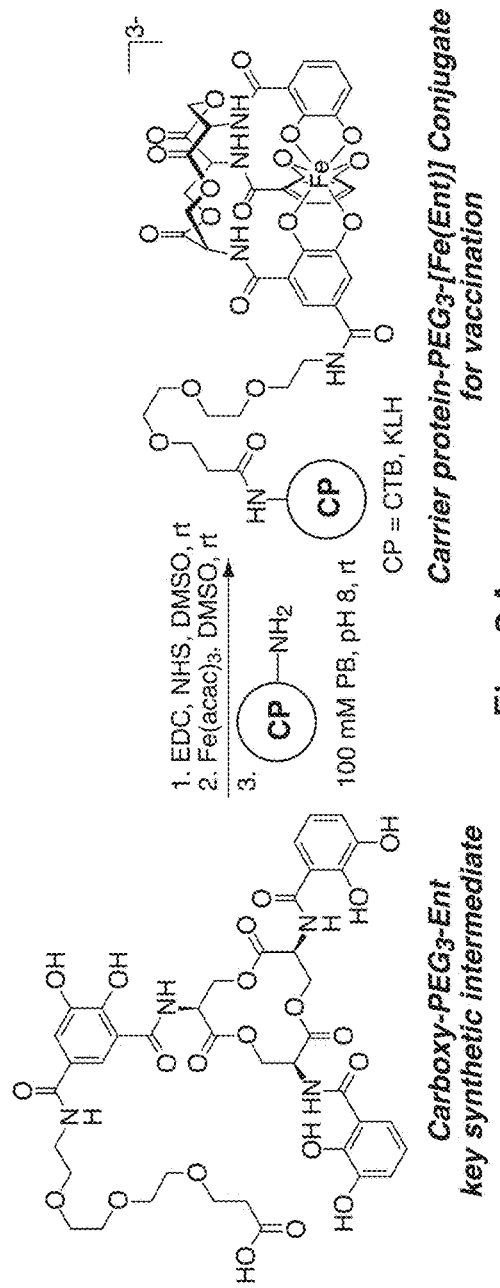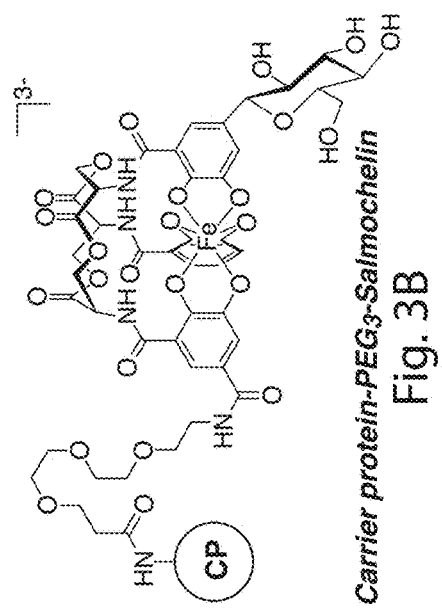
Fig. 3A — Carrier protein-PEG₃-[Fe(Ent)] Conjugate for vaccination
Fig. 3B — Carrier protein-PEG₃-Salmochelin
Carboxy-PEG₃-Ent key synthetic intermediate
1. EDC, NHS, DMSO, rt
2. Fe(acac)₃, DMSO, rt
3. 100 mM PB, pH 8, rt
CP = CTB, KLH

Strategy 1 for conjugate assembly:
Ent attachment using surface-exposed lysine residues of CTB
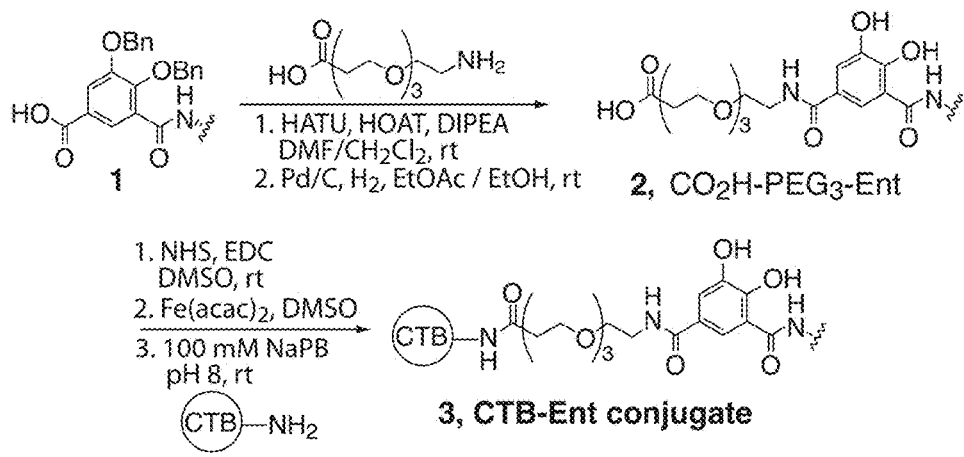
Fig. 5A
Strategy 2 for conjugate assembly:
Glu-Ent attachment using surface-exposed lysine residues of CTB
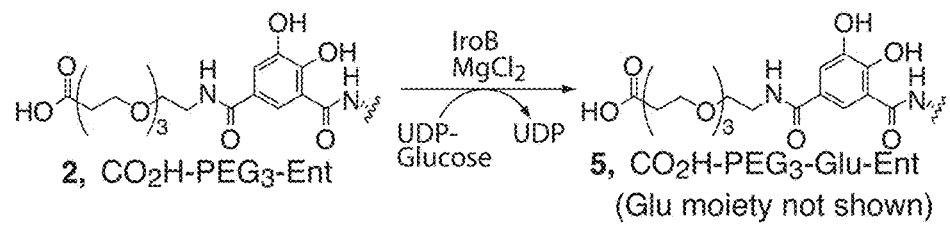
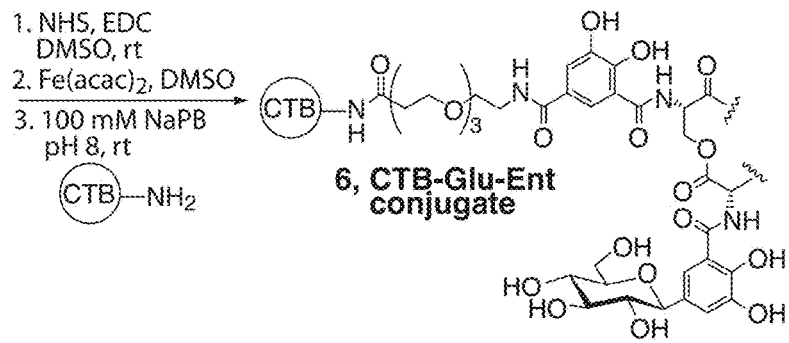
Fig. 5B

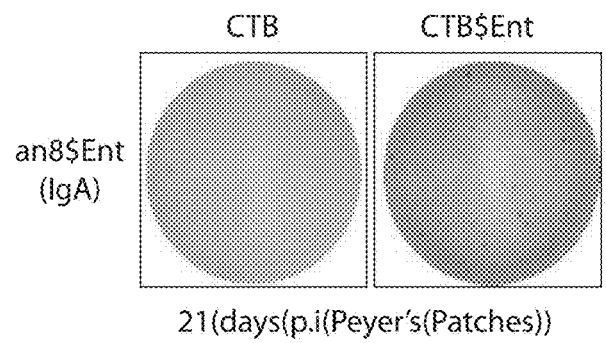
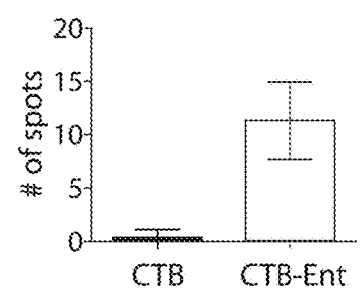
Fig. 8A                    Fig. 8B
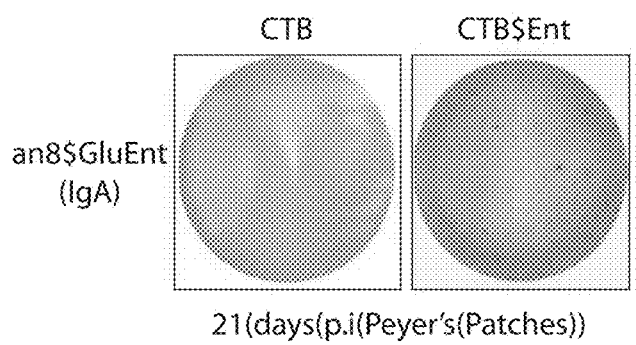
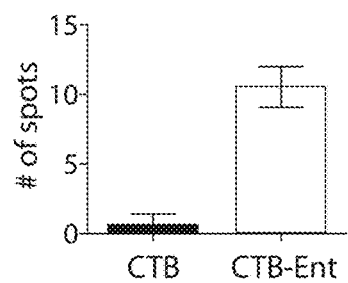
Fig. 8C                    Fig. 8D

SIDEROPHORE-BASED IMMUNIZATION AGAINST GRAM-NEGATIVE BACTERIA

RELATED APPLICATION

This application claims the benefit under 35 U.S.C. § 119(e) of U.S. provisional application Ser. No. 61/986,200, filed Apr. 30, 2014, the disclosures of which is incorporated by reference herein in its entirety.

GOVERNMENT SUPPORT

This invention was made with Government support under Grant Nos. AI065359, AI101784, and AI114625 awarded by the National Institutes of Health. The Government has certain rights in the invention.

BACKGROUND OF THE INVENTION

Iron (Fe) is an essential nutrient for almost all organisms. Enteric bacteria, including *Salmonella* and commensal/pathogenic *Escherichia coli*, require micromolar concentrations of Fe for replication and colonization in the vertebrate host. As levels of "free" Fe in the host are low, these bacteria biosynthesize and export small-molecule metal-ion chelators called "siderophores," which scavenge Fe from the host.

SUMMARY OF THE INVENTION

Of particular relevance is the interplay between the host protein lipocalin-2 (LCN2) and catecholate siderophores of the enterobactin (Ent) family (enterobactin, salmochelins), which are biosynthesized by Gram-negative bacteria including *Salmonella* and *E. coli*. The structures of these siderophores are given in FIG. 1. During bacterial infections, the mammalian host secretes LCN2 into the extracellular environment. LCN2 binds ferric Ent (the iron-bound form of Ent) with high affinity, and thereby blocks enterobactin-based iron acquisition by enterobactin-utilizing bacteria. LCN2 thereby inhibits bacteremia caused by commensal *E. coli* via iron deprivation. LCN2, however, is ineffective against *Salmonella* Typhimurium as well as certain pathogenic *E. coli*. These LCN2-resistant strains synthesize and secrete salmochelins, C-glucosylated derivatives of Ent (herein termed Glu-Ent) that are relatively hydrophilic and too large to fit into the Ent-binding pocket of LCN2. *Salmonella* and pathogenic *E. coli* overcome LCN2-dependent Fe starvation and thrives in the inflamed gut by utilizing Glu-Ent. Thus, Glu-Ent is an important virulence factor for *Salmonella*, promoting colonization and competition with the microbiota, and other pathogens.

Notably, a host-defense mechanism for blocking Glu-Ent-mediated Fe uptake by *Salmonella* and other microbes has not been identified. Because Fe acquisition enhances *Salmonella* intestinal colonization and competition with the microbiota, and the host itself cannot prevent Glu-Ent-mediated Fe uptake by this pathogen, one promising strategy to limit *Salmonella* infection is to block siderophore-mediated Fe acquisition by this bacterial species (FIG. 2). Improving upon the Fe-withholding strategy employed by the host will lead to innovative approaches to treat and prevent intestinal infection with *Salmonella*. Furthermore, this therapeutic strategy is expected to be applicable for other Ent/Glu-Ent utilizers such as pathogenic and commensal *E. coli*, both of which are associated with disease.

The invention provides immunization strategies to prevent the growth of non-typhoidal *Salmonella* and other enteric pathogens by blocking the acquisition of the essential nutrient iron. Applications include vaccination of livestock and the treatment of humans, in which *Salmonella* causes foodborne illness. Towards this purpose, the invention includes: (i) the design and preparation of immunogenic protein-enterobactin/salmochelin conjugates; (ii) ELISA assays for detecting antibodies to enterobactin/salmochelin; (iii) ELISPOT protocols for detecting antibodies for enterobactin and salmochelin; (iv) mucosal immunization strategies; and (v) therapeutic antibody development.

The present invention provides novel enterobactin-carrier protein conjugates and salmochelin-carrier protein conjugates such as compounds of Formula (I), and salts, hydrates, solvates, polymorphs, co-crystals, tautomers, stereoisomers, and isotopically labeled derivatives thereof:

$$\text{CP-(L-Ent)}_n \quad\quad\quad (I)$$

wherein CP (carrier protein), L, and n are as described herein, and Ent represents enterobactin, salmochelin (Glu-Ent), a hydrolyzed enterobactin or salmochelin analog or a non-hydrolyzable enterobactin or salmochelin analog. In some embodiments, L-Ent is attached to one or more lysine residues on the carrier protein. In some embodiments, the Ent is complexed with iron, i.e., is ferric enterobactin (FeEnt), ferric salmochelin, or an analog thereof.

Hydrolyzed enterobactin analogs include linear Ent, 2,3-dihydroxybenzyl serine (DHBS) monomer and dimer, and glucosylated forms thereof. See FIG. 1, which shows the structures of several of these analogs.

Non-hydrolyzable enterobactin analogs include: cationic analogs of enterobactin such as tris catecholate analogs lacking macrolactone (see Rodgers et al. Inorg Chem. 1987; 26(10):1622-5; Tor et al. J Am Chem Soc. 1992; 114(17): 6653-61; Ecker et al. J Am Chem Soc. 1988; 110(8):2457-64; Stack et al. J Am Chem Soc. 1993; 115(14):6466-7; Ji et al. J Am Chem Soc. 2012; 134(24):9898-901).

Carrier proteins include: keyhole limpet hemocyanin (KLH), ovalbumin (OVA), cholera toxin B subunit (CTB), *Concholepas concholepas* hemocyanin (CCH) and bovine serum albumin (BSA).

Linkers are described in more detail below. In some embodiments, a linker is a poly(ethylene glycol) (PEG) molecule, such as a PEG molecule having 1-10 subunits, such as a PEG molecule having 3 subunits (a $PEG_3$ molecule).

In some embodiments, one L-Ent is attached to each carrier protein, i.e., n=1. In some embodiments, more than one L-Ent is attached to each carrier protein, i.e., n is greater than 1. Thus n can be an integer such as 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 120, 140, 160, 180, 200, 220, 240, 260, 280, 300, 320, 340, 360, 380, 400 or more, such that one or more than one L-Ent is attached to each carrier protein. For example, n can be 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-100, 10-100, 20-100, 30-100, 40-100, 50-100, 60-100, 70-100, 80-100, 90-100, 5-200, 10-200, 20-200, 30-200, 40-200, 50-200, 60-200, 70-200, 80-200, 90-200, 100-200, 5-300, 10-300, 20-300, 30-300, 40-300, 50-300, 60-300, 70-300, 80-300, 90-300, 100-300, 5-400, 10-400, 20-400, 30-400, 40-400, 50-400, 60-400, 70-400, 80-400, 90-400, 100-400, etc. While it is also possible that less than one CP can be attached to a single L-Ent moiety (i.e., n<1, such as n=½ where two CP are attached to one L-Ent), such arrangements may be less preferred.

In another aspect, the present invention provides compositions (e.g., pharmaceutical compositions or diagnostic compositions) including a compound of Formula (I), and optionally an excipient. In certain embodiments, the compositions are useful in inducing an immune response against enterobactin or salmochelin, or an analog thereof.

A composition may be a pharmaceutical composition. In certain embodiments, a pharmaceutical composition of the invention includes a therapeutically or prophylactically effective amount of a compound of Formula (I), or a pharmaceutically acceptable salt thereof. The pharmaceutical composition may be useful for treating and/or preventing a bacterial infection and/or inflammatory bowel disease (IBD) in a subject in need thereof, inhibiting the growth of a bacterium, and/or killing a bacterium.

Another aspect of the present invention relates to methods of inducing an immune response against an enterobactin or salmochelin molecule including administering to a subject an amount of the compound of Formula (I), or a pharmaceutically acceptable salt thereof, or a pharmaceutical composition thereof effective to induce an immune response against the enterobactin or salmochelin molecule in Formula (I), or an analog thereof. Inducing an immune response can include vaccination with the compound of Formula (I) to induce an immune response before infection with a bacteria that produces an enterobactin or salmochelin molecule as contained the compound of formula (I), and thus to provide protective immunity against such bacteria. The subject in whom an immune response is induced can be one who is infected with, suspected of being infected with, or at risk of being infected with a bacteria that produces an enterobactin or salmochelin molecule as contained the compound of Formula (I).

Another aspect of the present invention relates to methods of treating a bacterial infection and/or IBD in a subject in need thereof, the method including administering to the subject a therapeutically effective amount of a compound of Formula (I), or a pharmaceutically acceptable salt thereof, or a pharmaceutical composition thereof.

Another aspect of the present invention relates to methods of preventing a bacterial infection and/or IBD in a subject in need thereof, the method including administering to the subject a prophylactically effective amount of a compound of Formula (I), or a pharmaceutically acceptable salt thereof, or a pharmaceutical composition thereof.

In certain embodiments, the subject is a human. In certain embodiments, the subject is a non-human mammal. In certain embodiments, the bacterium is a Gram-negative bacterium. In certain embodiments, the bacterial infection is an infection caused by a Gram-negative bacterium.

Another aspect of the present invention relates to kits comprising a container with a compound described herein or a composition described herein. The kits of the invention may include a single dose or multiple doses of the compound or composition. The provided kits may be useful in inducing an immune response, treating a bacterial infection and/or IBD in a subject in need thereof, preventing a bacterial infection and/or IBD in a subject in need thereof, inhibiting the growth of a bacterium, or killing a bacterium. In certain embodiments, a kit further includes instructions for using the kit.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 3A and FIG. 3B show an overview of the carrier protein (CP) enterobactin/salmochelin conjugates. FIG. 3A: Generalized synthesis of a conjugate between a CP (e.g., CTB, KLH) and Ent. FIG. 3B: Target structure of a conjugate between a CP and a salmochelin (Glu-Ent) based on the CP-Ent conjugates shown in FIG. 3A. The monoglucosylated version is shown as an example and the diglucosylated form can also be invisioned.

FIG. 5A shows Strategy 1, which is the strategy for preparing CTB-Ent (see FIG. 4). FIG. 5B and FIG. 5C, respectively, show Strategies 2 and 3, which are routes for the preparation of Glu-Ent versions.

FIG. 7A: Detection of fecal Ent-IgA in mice immunized with either CTB (n=5) or CTB-Ent (n=7). The fecal Ent-IgA was quantified by using the in-house ELISA ( pvalue <0.05). FIG. 7B: DOTBLOT for detection of anti-siderophore antibodies. Ent (1 µg) or DGE (1 g, also abbreviated as Glu-Ent) was spotted on a PVDF membrane and CTB-Ent fecal extract (day 21 post-immunization) was used to detect specific IgA anti-Ent and anti-Glu-Ent. FIG. 7C: ELISA for detection of fecal Ent-IgA in mice immunized with either CTB (n=15-20) or CTB-Ent (n=15-20) (Day 21). FIG. 7D: ELISA for detection of fecal Glu-Ent-IgA in mice immunized with either CTB (n=15-20) or CTB-Ent (n=15-20) (day 21) ( pvalue <0.0001, * pvalue <0.001, **pvalue <0.01).

FIGS. 8A-8D show ELISPOT assays employing B cells to detect immunocomplexes (spots). FIG. 8A: Representative Images from an ELISPOT assay. Detection of Ent-IgA from Peyer's patches of mice immunized with either CTB or CTB-Ent (Day 21). FIG. 8B: Average of number of spots detected in CTB or CTB-Ent immunized mice (n=7 mice). FIG. 8C: Representative Images from an ELISPOT assay. Detection of Glu-Ent-IgA from Peyer's patches of mice immunized with either CTB or CTB-Ent (Day 21). FIG. 8D: Number of spots Average of number of spots detected in CTB or CTB-Ent immunized mice (n=5 mice).

represent CTB-Ent immunized mice that were monitored for 6 days post-infection. (** pvalue <0.0001, * pvalue <0.001).

Figure 7A:
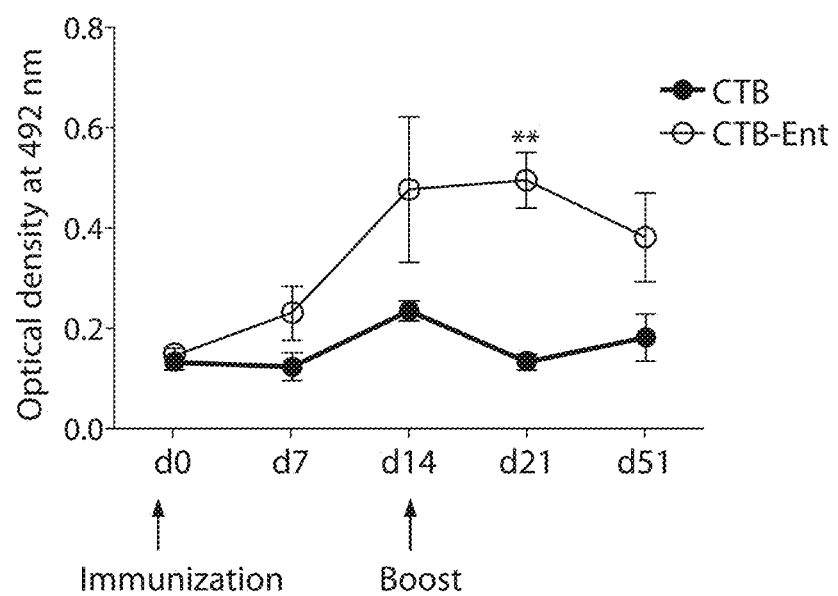
FIGS. 7A-7D show detection of anti-siderophore antibodies.
Figure 7B:
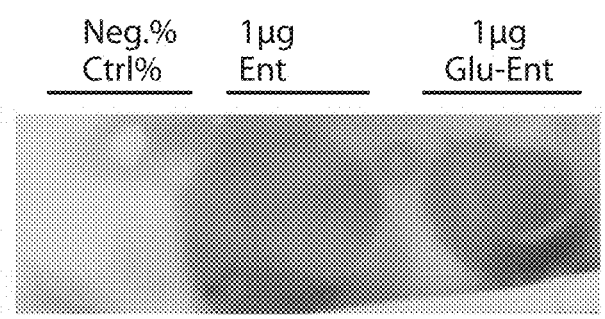
Figure 7C:
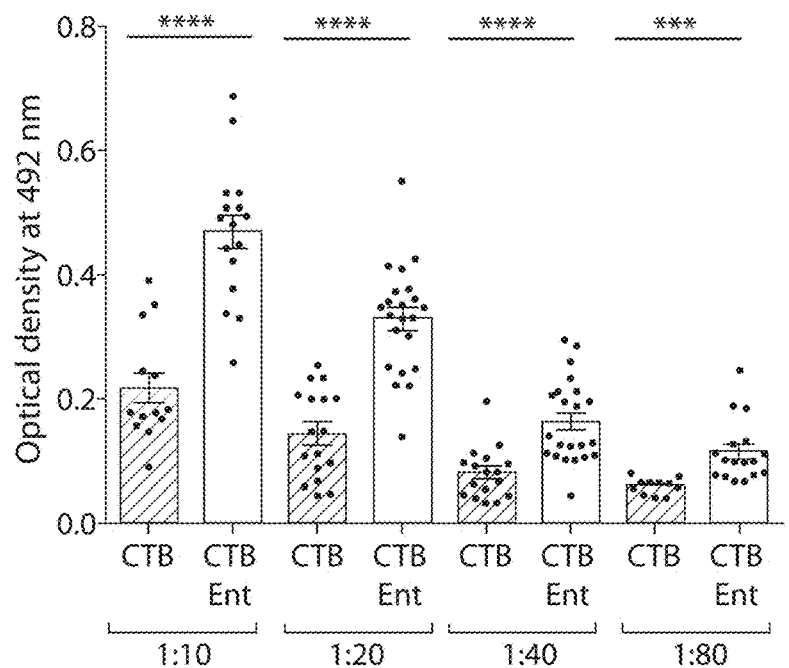
Figure 9:
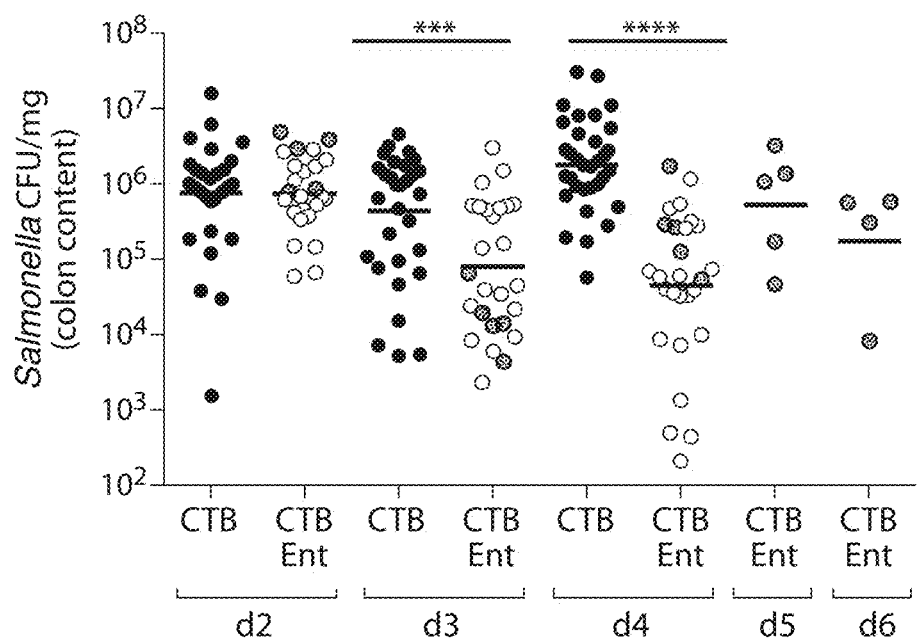
FIG. 9 shows bacterial load in the colon of immunized mice infected with *Salmonella*. CTB immunized mice (black dots, n=35) and CTB-Ent immunized mice (white and grey dots, n=27) at day 2 to day 6 post-infection. Grey dots (n=5)
Figure 10:
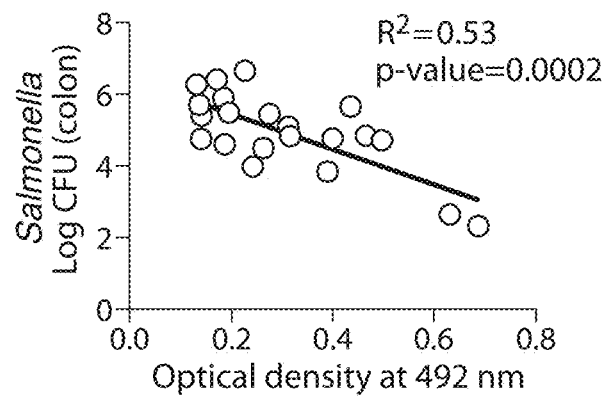

FIG. 10 shows correlation of *Salmonella* CFU (colon content at day 4 post-infection, FIG. 9) and specific Ent-IgA (n=21) detected by ELISA assay (FIG. 7C).

Figure 11A:
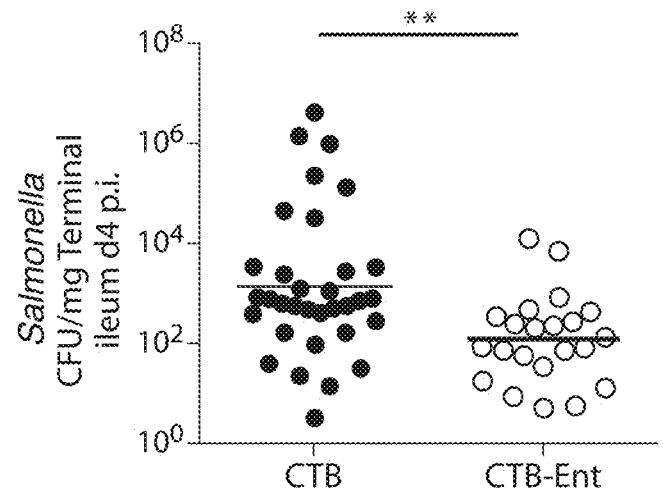
Figure 11B:
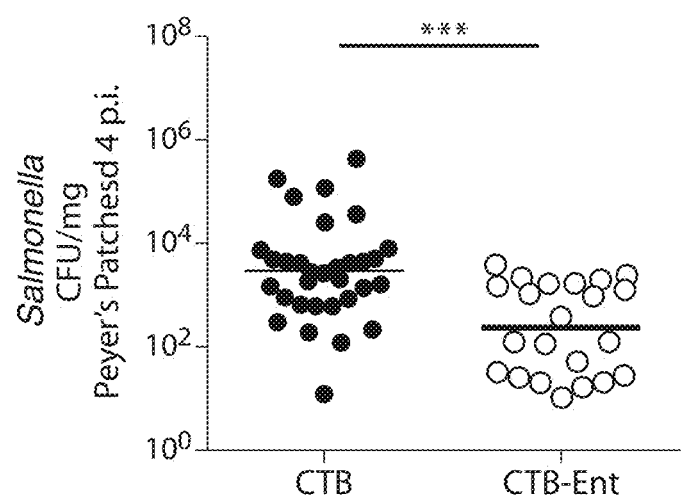

FIGS. 11A and 11B show bacterial load in immunized mice infected with *Salmonella*. FIG. 11A: *Salmonella* colonization (CFU/mg) of the terminal ileum. FIG. 11B: *Salmonella* colonization (CFU/mg) of the Peyer's patches. CTB immunized mice (black dots, n=33) and CTB-Ent immunized mice (white dots, n=22) (* pvalue <0.001,  pvalue <0.01).

Figure 12A:
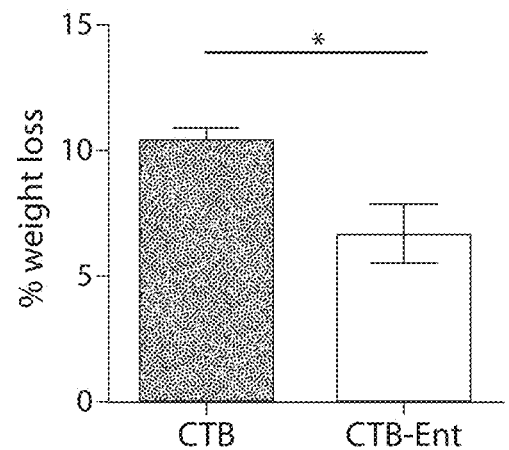
Figure 12B:
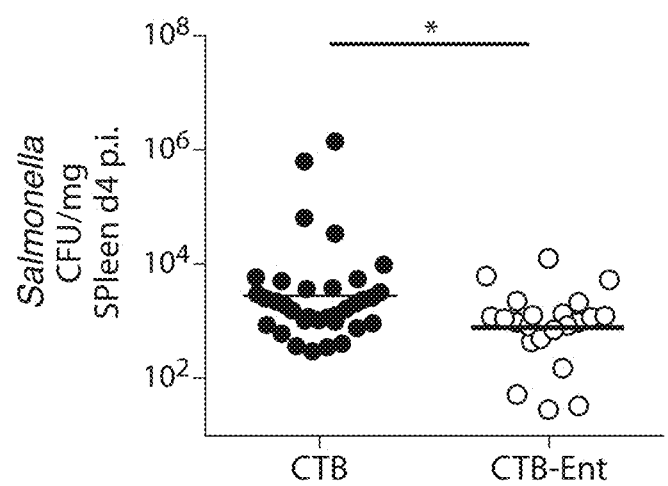

FIGS. 12A and 12B show *Salmonella* dissemination and disease. FIG. 12A: Weight loss in CTB (black bars, n=22) and CTB-ENT (white bars, n=13) immunized mice at day 4 post-infection. FIG. 12B: *Salmonella* colonization (CFU/mg) in the spleen. CTB-immunized mice (black dots, n=33) and CTB-Ent immunized mice (white dots, n=22) (* pvalue <0.05).

Figure 13A:
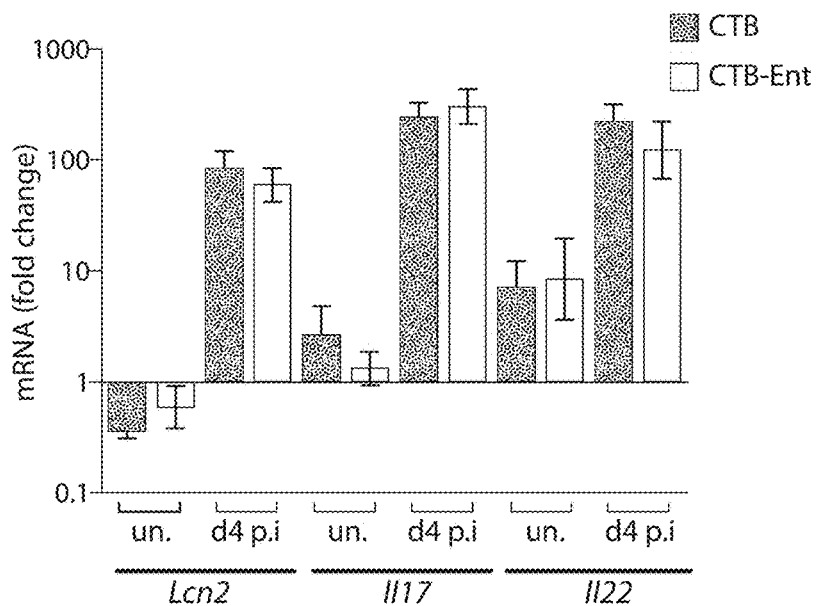
Figure 13B:
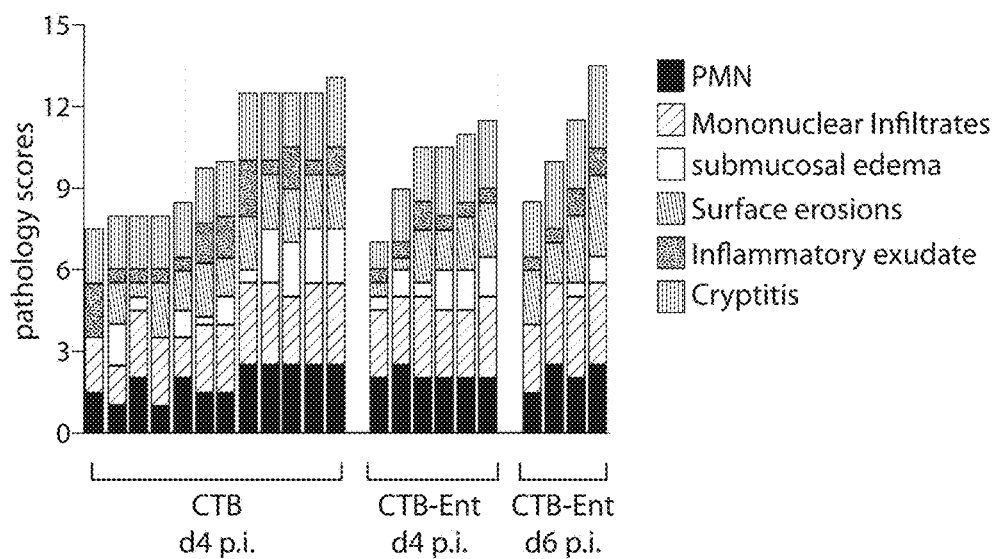

FIGS. 13A and 13B show host response in CTB and CTB-Ent immunized mice. FIG. 13A: Lipocalin-2 (Lcn2) and pro-inflammatory cytokines expression in CTB and CTB-EnT mice uninfected (uninfected, n=5) or at day 4 post-infection (n=12). FIG. 13B: Pathology scores in CTB and CTB-Ent mice at day 4 post-infection or day 6 post-infection.

Figure 14A:
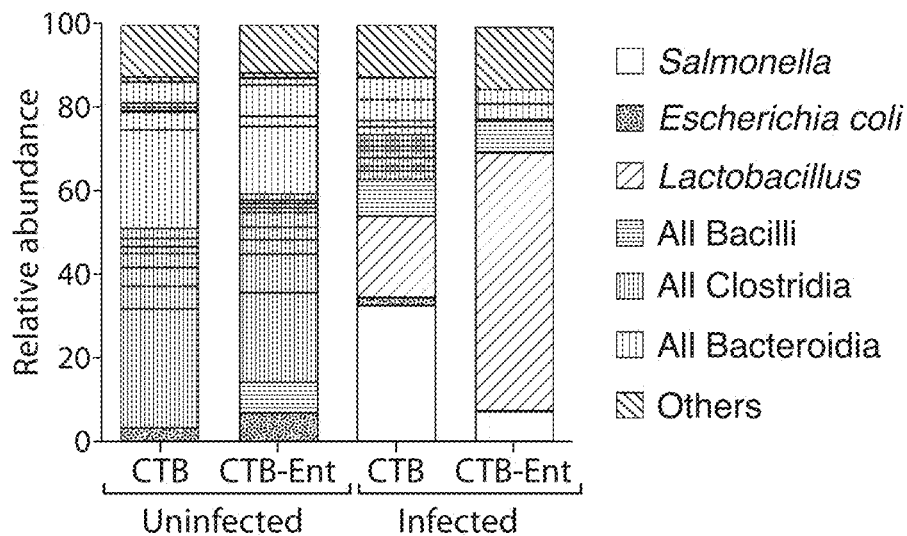
Figure 14B:
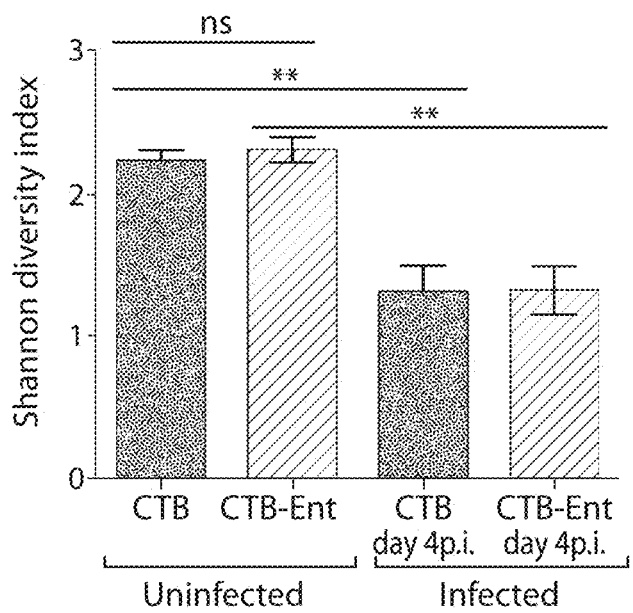
Figure 14C:
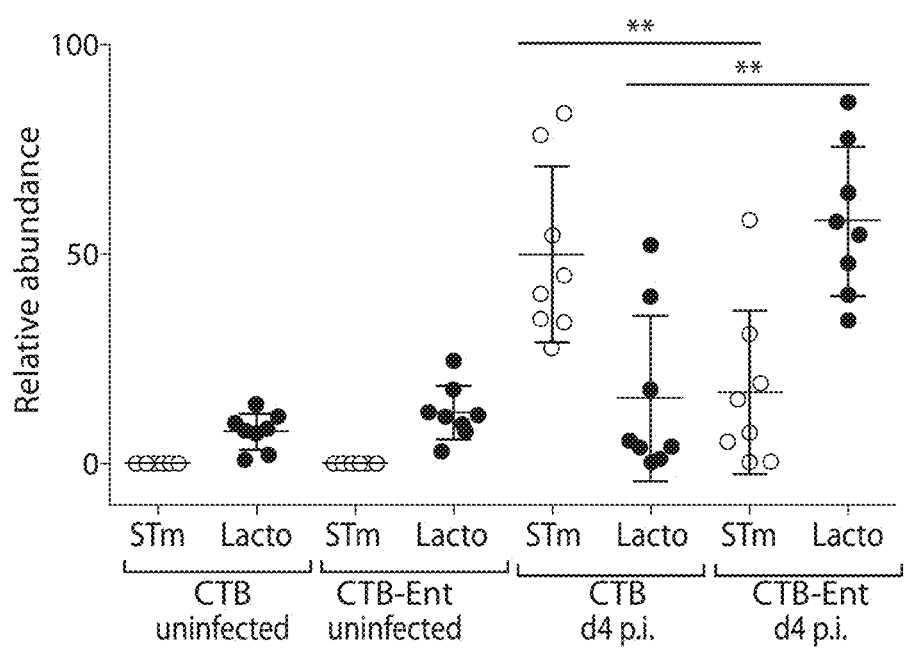

FIGS. 14A-14C show analysis of the microbiota in immunized mice (Illumina MiSeq). FIG. 14A: Stool samples from CTB and CTB-Ent immunized mice were collected before (uninfected, n=5) and at day 4 post-infection (infected, n=5) to analyze the microbiota composition. FIG. 14B: Bacterial diversity in each group measured by Shannon diversity index. FIG. 14C: Statistical analysis of *Salmonella* (ST) and *Lactobacillus* (Lacto) numbers measured by Illumina MiSeq before and at day 4 post-infection (** pvalue <0.01).

Figure 4:
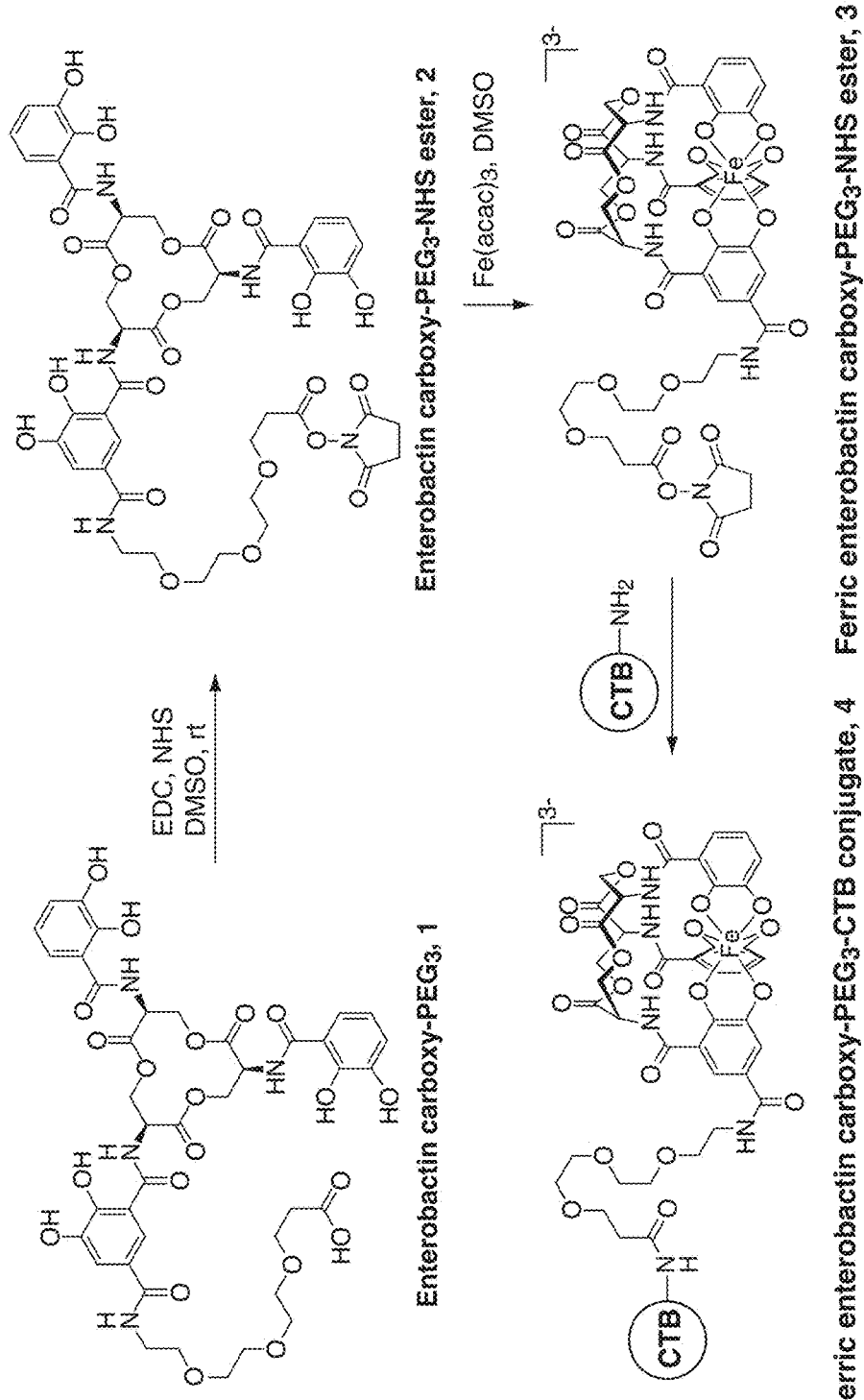
FIG. 4 shows an optimized preparation of CTB-Ent.
Figure 5C:
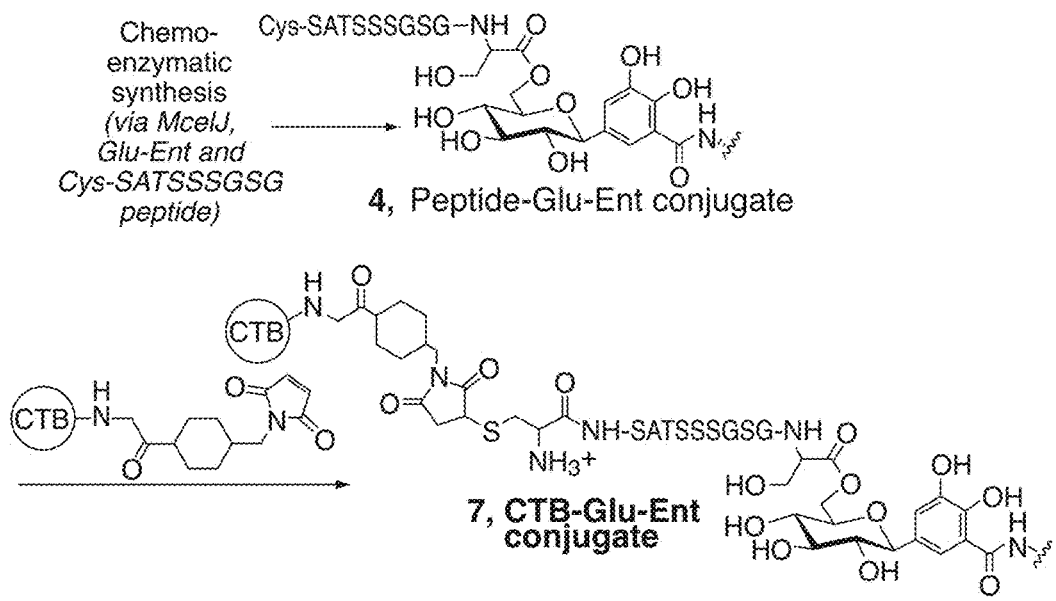
Figure 15A:
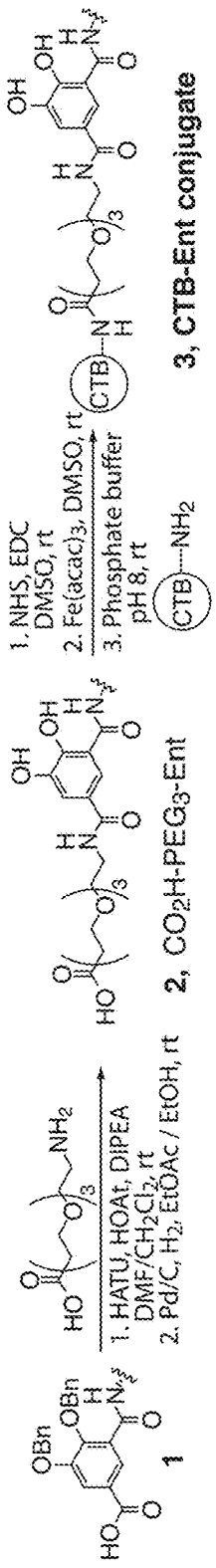
Figure 15B:
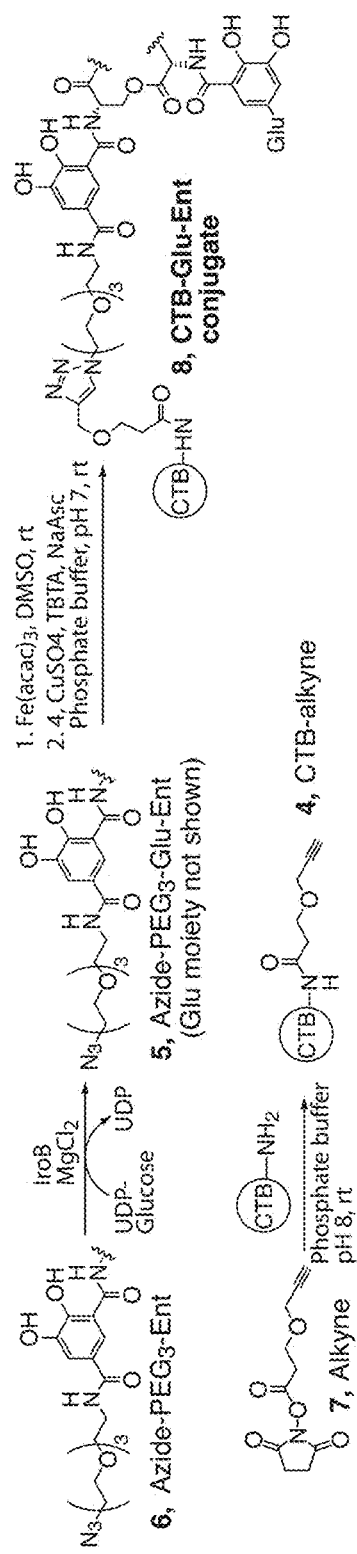
Figure 15C:
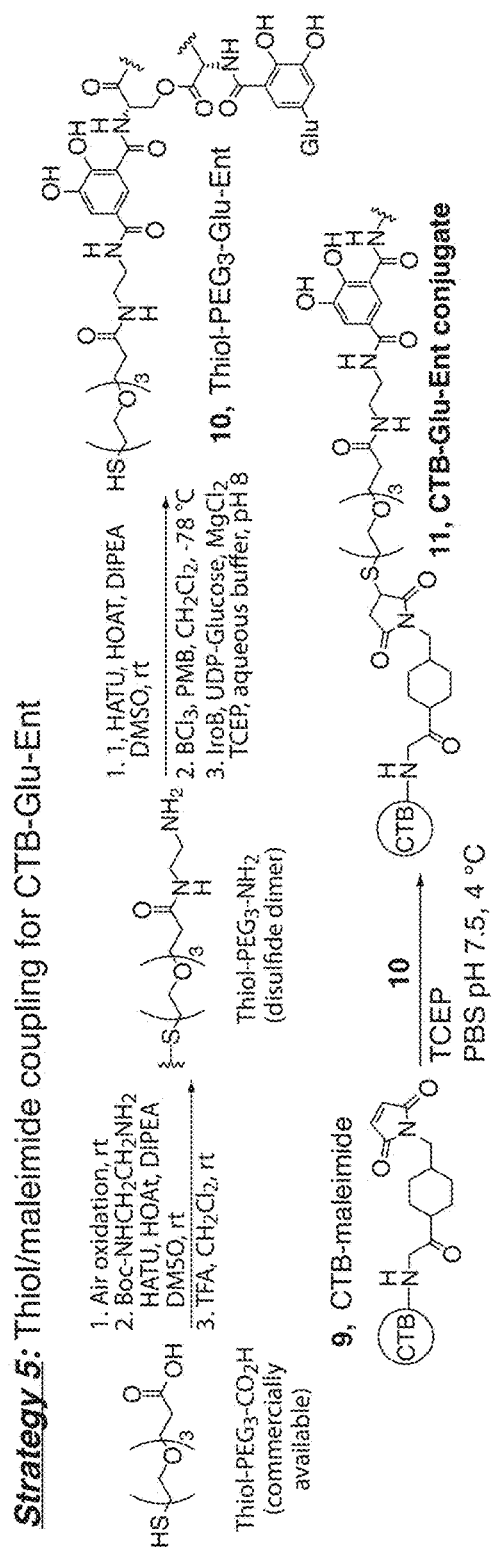

FIG. 15A shows Strategy 1, which is a strategy for preparing CTB-Ent (see also FIG. 4 and FIG. 5A). FIG. 15B and FIG. 15C show alternative preparative strategies (Strategies 4 and 5, respectively) for the preparation of Glu-Ent analogues.

Figure 16:
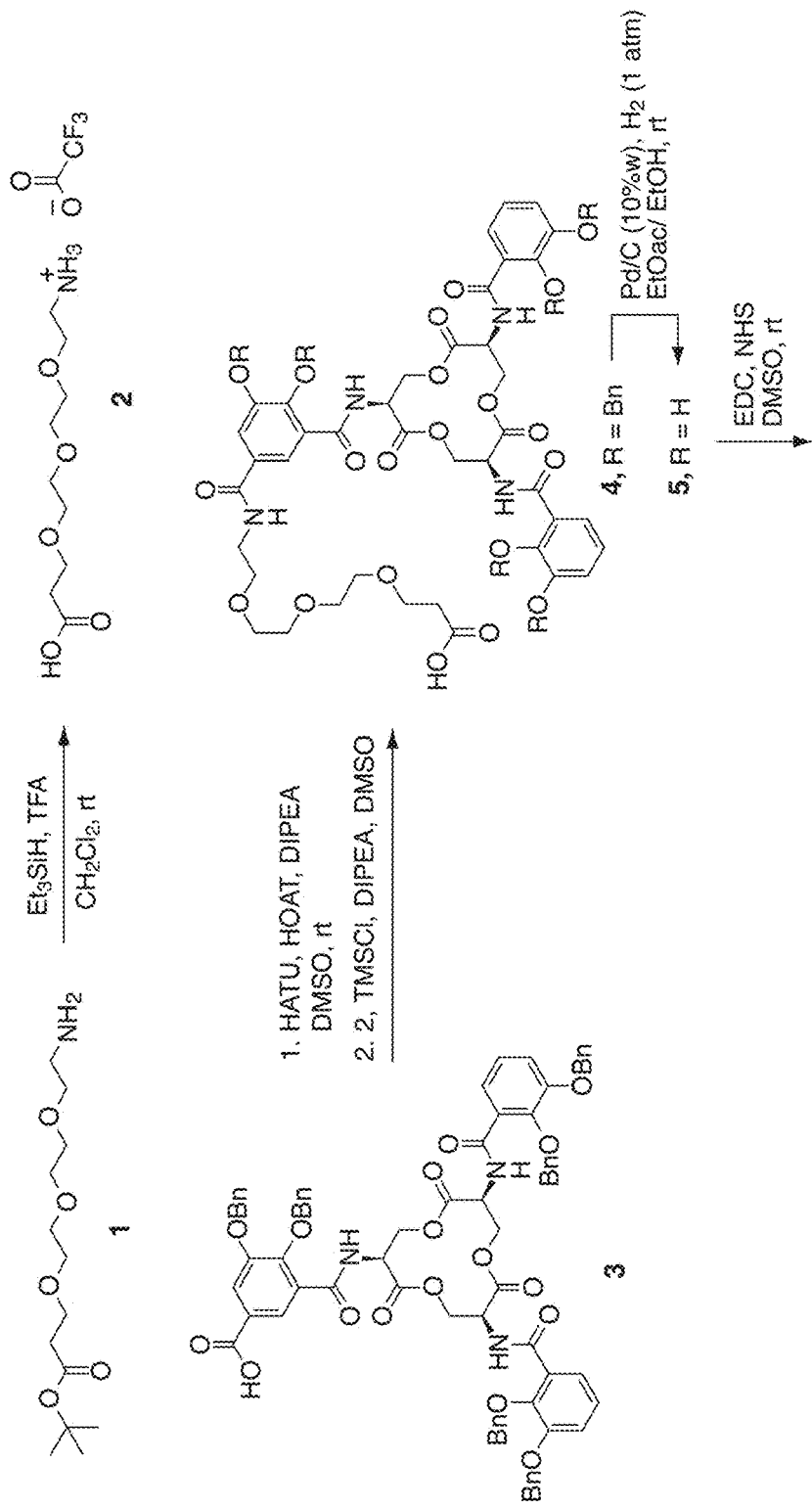
Figure 16:
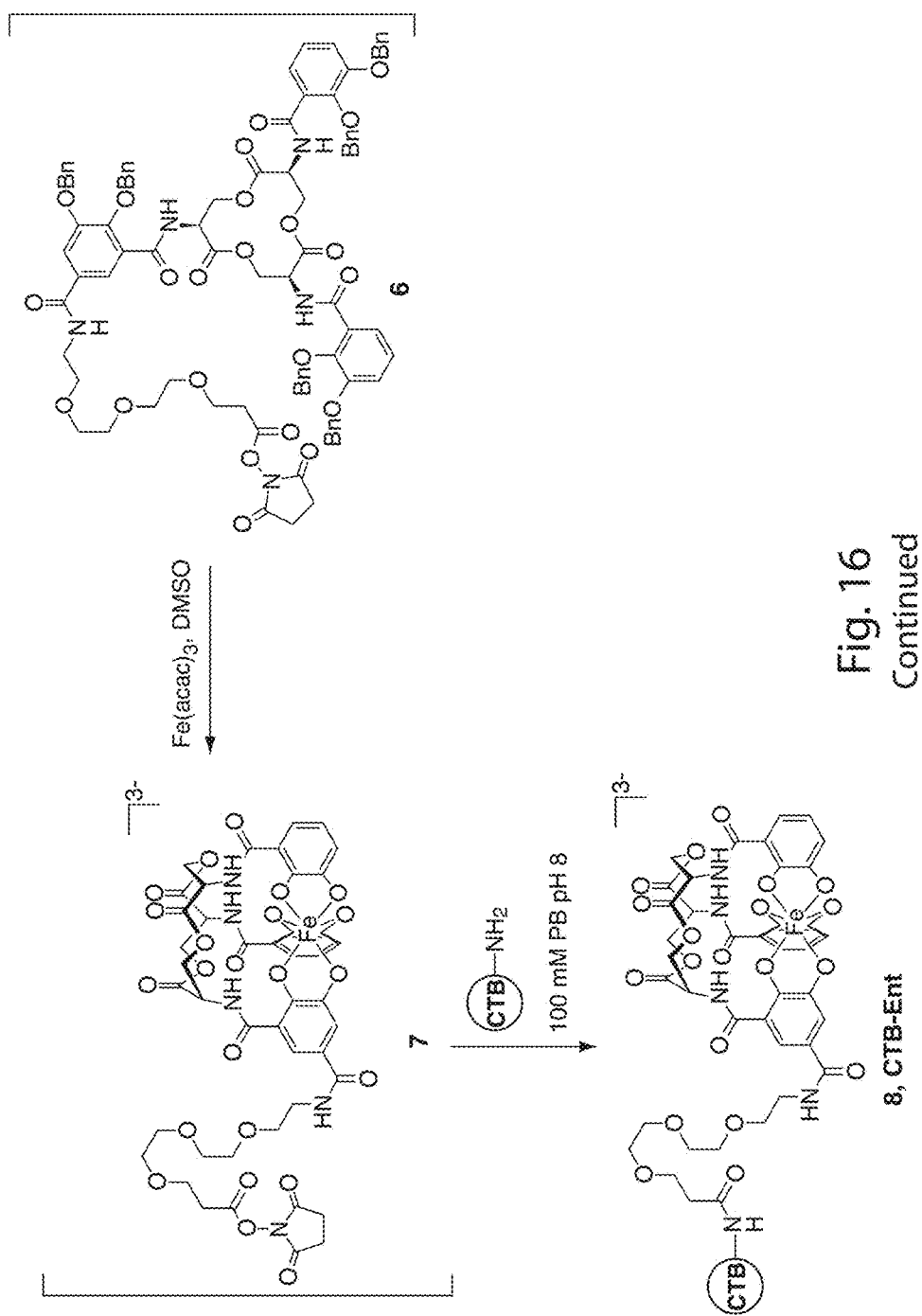

FIG. 16 shows more detail of synthesis of a CTB-Ent conjugate.

Figure 17A:
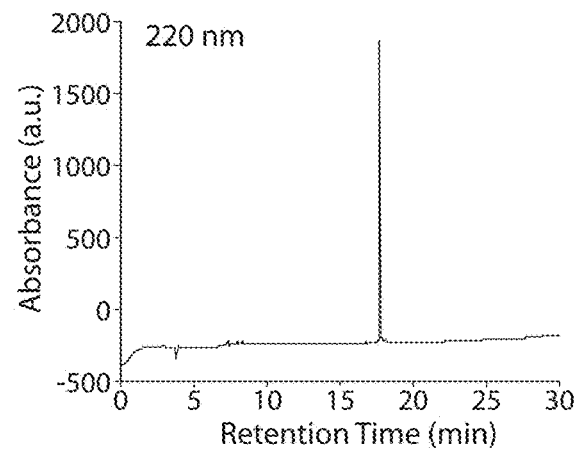
Figure 17B:
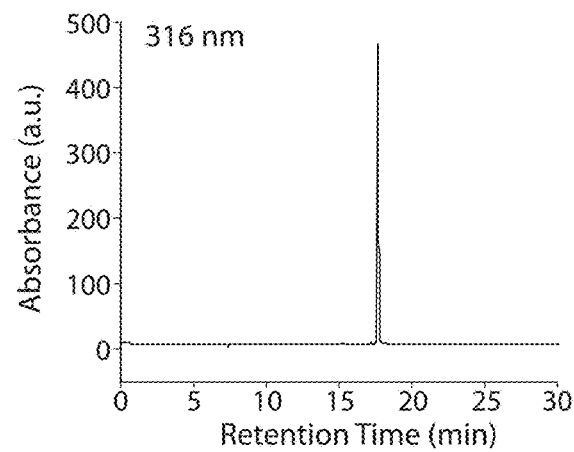

FIGS. 17A and 17B show analytical HPLC traces (FIG. 17A) 220 nm and (FIG. 17B) 316 nm (0-100% B over 30 min, 1 mL/min) of Ent-PEG3 acid 5.

Figure 18:
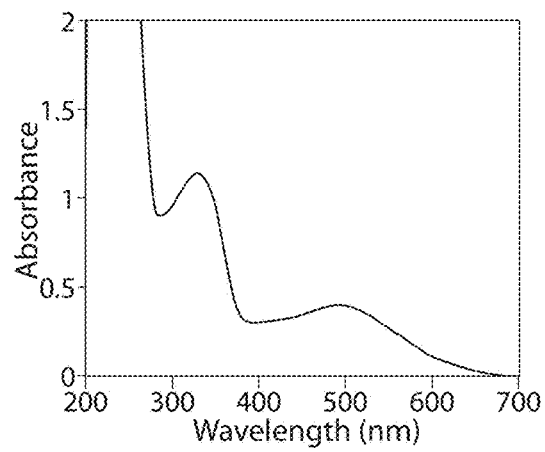

FIG. 18 shows a UV-visible spectrum of CTB-Ent 8 in PBS pH 7.2.

Figure 19:
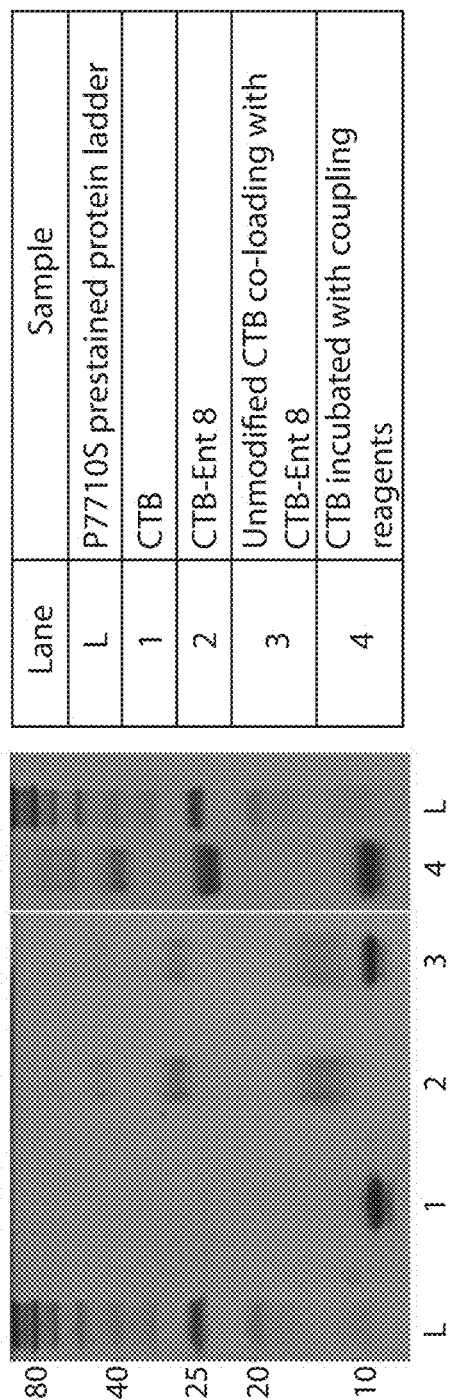

FIG. 19 shows SDS-PAGE (16% tricine) of samples from coupling reactions performed under the conditions described in the table. Unmodified CTB is 11.6 kDa and Ent-PEG3 acid B is approximately 900 Da.

DETAILED DESCRIPTION OF CERTAIN EMBODIMENTS OF THE INVENTION

Bacteria cannot easily modify siderophores because complex gene clusters are required for siderophore biosynthesis and utilization. This feature makes the siderophores attractive targets for vaccine development. Prior studies by others have addressed making vaccines against outer membrane receptors such as FepA. While partly successful, this receptor-based approach has at least two potential pitfalls: (i) potential misfolding of the overexpressed outer membrane receptors used for antibody generation may account for the poor immunogenicity/limited efficacy; (ii) outer membrane proteins may be modified by pathogens to evade the immune response by simply mutating a few amino acids.

One of the biggest hurdles in developing vaccines against *Salmonella* is their great diversity in the O and H antigens, resulting in approximately 2,500 serotypes of non-typhoidal *Salmonella* that cause inflammatory diarrhea. All *Salmonella* synthesize and utilize enterobactin and salmochelins for iron acquisition. Antibodies and induced immune responses against enterobactin and salmochelins (including by vaccination) will therefore be active against multiple *Salmonella* serotypes. This generality is a major advantage over traditional vaccines.

Similarly, other pathogens (including *Escherichia coli* and *Klebsiella pneumoniae*) need enterobactin and salmochelin to acquire iron. Inducing an immune response (including by vaccination) and/or administration of therapeutic antibodies may reduce the growth of these pathogens in sites like the intestine, the urinary tract, and the lungs.

Antibodies induced or produced against the conjugates described herein will likely target only Enterobacteriaceae, but in contrast to broad spectrum antibiotics will not affect a large portion of the intestinal microbiota, which is largely comprised by Bacteroidetes and Firmicutes. Experimental results described herein demonstrate that the effect on the microbiota may actually be beneficial, as an increased growth of *Lactobacillus* spp was observed in mice immunized with the enterobactin conjugate.

An additional advantage of the conjugates described herein is for use in treating inflammatory bowel disease (IBD). One of the pathobionts (e.g., a commensal strain with potential to cause disease) commonly isolated from patients with IBD is the *E. coli* strain LF82, which secretes both enterobactin and salmochelin. This strain is considered one of the potential triggers/perpetuators of inflammation in IBD. Therefore IBD patients that are positive for LF82 could potentially benefit from either inducing an immune response using the conjugates described herein (including vaccination) or the administration of therapeutic antibodies produced using the conjugates described herein. At present, there are no therapies to modulate the microbiota in IBD.

Thus the present invention provides novel enterobactin-carrier protein conjugates, such as compounds of Formula (I), and salts thereof. The present invention also provides compositions, kits, and methods that involve the compounds of Formula (I) and are useful inducing an immune response, treating a bacterial infection and/or inflammatory bowel disease (IBD) in a subject, preventing a bacterial infection and/or IBD in a subject, or inhibiting the growth of or killing a bacterium. In certain embodiments, the bacterium is a Gram-negative bacterium.

Uses and embodiments of aspects of the invention include vaccination of livestock and humans against *Salmonella*; producing therapeutic antibodies for treating *Salmonella* infection in humans or other animals; vaccination of humans against inflammatory bowel disease (*E. coli* LF82 and similar); producing therapeutic antibodies for treating humans for inflammatory bowel disease (*E. coli* LF82 and similar); vaccination of humans against disease caused by *E. coli* and *Klebsiella* (including urinary tract infections, lung infections); producing therapeutic antibodies for treating humans for disease caused by *E. coli* and *Klebsiella* (including urinary tract infections, lung infections); and producing antibodies for treatment of fecal material before fecal microbiota transplant (FMT).

Additional uses and embodiments of aspects of the invention include ELISA assays for detecting antibodies to enterobactin or salmochelin, or an analog thereof, and ELISPOT assays, such as for detecting whether specific B cells producing antibodies to enterobactin or salmochelin, or an analog thereof, develop upon infection/immunization.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)- isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched" means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}$C or $^{14}$C are within the scope of this invention. Such compounds are useful, for example, as analytical tools, as probes in biological assays, or as therapeutic agents in accordance with the present invention.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic" includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl" denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)

$OR^{aa}$, $-OC(=NR^{bb})R^{aa}$, $-OC(=NR^{bb})OR^{aa}$, $-C(=NR^{bb})N(R^{bb})_2$, $-OC(=NR^{bb})N(R^{bb})_2$, $-NR^{bb}C(=NR^{bb})N(R^{bb})_2$, $-C(=O)NR^{bb}SO_2R^{aa}$, $-NR^{bb}SO_2R^{aa}$, $-SO_2N(R^{bb})_2$, $-SO_2R^{aa}$, $-SO_2OR^{aa}$, $-OSO_2R^{aa}$, $-S(=O)R^{aa}$, $-OS(=O)R^{aa}$, $-Si(R^{aa})_3$, $-OSi(R^{aa})_3$, $-C(=S)N(R^{bb})_2$, $-C(=O)SR^{aa}$, $-C(=S)SR^{aa}$, $-SC(=S)SR^{aa}$, $-SC(=O)SR^{aa}$, $-OC(=O)SR^{aa}$, $-SC(=O)OR^{aa}$, $-SC(=O)R^{aa}$, $-P(=O)_2R^{aa}$, $-OP(=O)_2R^{aa}$, $-P(=O)(R^{aa})_2$, $-OP(=O)(R^{aa})_2$, $-OP(=O)(OR^{cc})_2$, $-P(=O)_2N(R^{bb})_2$, $-OP(=O)_2N(R^{bb})_2$, $-P(=O)(NR^{bb})_2$, $-OP(=O)(NR^{bb})_2$, $-NR^{bb}P(=O)(OR^{cc})_2$, $-NR^{bb}P(=O)(NR^{bb})_2$, $-P(R^{cc})_2$, $-P(R^{cc})_3$, $-OP(R^{cc})_2$, $-OP(R^{cc})_3$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN(R^{bb})_2, =NNR^{bb}C(=O)R^{aa}, =NNR^{bb}C(=O)OR^{aa}, =NNR^{bb}S(=O)_2R^{aa}, =NR^{bb}, or =NOR^{cc};

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_1$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl)$_2$, $-N(C_{1-6}$ alkyl)$_2$, $-N(C_{1-6}$ alkyl)$_3^+X^-$, $-NH(C_{1-6}$ alkyl)$_2^+X^-$, $-NH_2(C_{1-6}$ alkyl)$^+X^-$, $-NH_3^+X^-$, $-N(OC_{1-6}$ alkyl)($C_{1-6}$ alkyl), $-N(OH)(C_{1-6}$ alkyl), $-NH(OH)$, $-SH$, $-SC_{1-6}$ alkyl, $-SS(C_{1-6}$ alkyl), $-C(=O)(C_{1-6}$ alkyl), $-CO_2H$, $-CO_2(C_{1-6}$ alkyl), $-OC(=O)(C_{1-6}$ alkyl), $-OCO_2(C_{1-6}$ alkyl), $-C(=O)NH_2$, $-C(=O)N(C_{1-6}$ alkyl)$_2$, $-OC(=O)NH(C_{1-6}$ alkyl), $-NHC(=O)(C_1$ alkyl), $-N(C_{1-6}$ alkyl)C(=O)(C_1$ alkyl), $-NHCO_2(C_{1-6}$ alkyl), $-NHC(=O)N(C_{1-6}$ alkyl)$_2$, $-NHC(=O)NH(C_{1-6}$ alkyl), $-NHC(=O)NH_2$, $-C(=NH)O(C_{1-6}$ alkyl), $-OC(=NH)(C_{1-6}$ alkyl), $-OC(=NH)OC_{1-6}$ alkyl, $-C(=NH)N(C_{1-6}$ alkyl)$_2$, $-C(=NH)NH(C_{1-6}$ alkyl), $-C(=NH)NH_2$, $-OC(=NH)N(C_{1-6}$ alkyl)$_2$, $-OC(NH)NH(C_{1-6}$ alkyl), $-OC(NH)NH_2$, $-NHC(NH)N(C_{1-6}$ alkyl)$_2$, $-NHC(=NH)NH_2$, $-NHSO_2(C_1$ alkyl), $-SO_2N(C_{1-6}$ alkyl)$_2$, $-SO_2NH(C_{1-6}$ alkyl), $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl)$_3$, $-OSi(C_{1-6}$ alkyl)$_3$, $-C(=S)N(C_{1-6}$ alkyl)$_2$, $C(=S)NH(C_{1-6}$ alkyl), $C(=S)NH_2$, $-C(=O)S(C_{1-6}$ alkyl), $-C(=S)SC_{1-6}$ alkyl, $-SC(=S)SC_{1-6}$ alkyl, $-P(=O)_2(C_{1-6}$ alkyl), $-P(=O)(C_{1-6}$ alkyl)$_2$, $-OP(=O)(C_{1-6}$ alkyl)$_2$, $-OP(=O)(OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "amino" refers to a group of the formula ($-NH_2$). A "substituted amino" refers either to a monosubstituted amine ($-NHR^h$) of a disubstituted amine ($-NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group (—$NR^h{}_2$) form a 5- to 6-membered heterocyclic ring.

The term "alkoxy" refers to a "substituted hydroxyl" of the formula (—$OR^i$), wherein $R^i$ is an optionally substituted alkyl group as defined herein, and the oxygen moiety is directly attached to the parent molecule.

The term "alkylthioxy" refers to a "substituted thiol" of the formula (—$SR^r$), wherein $R^r$ is an optionally substituted alkyl group as defined herein, and the sulfur moiety is directly attached to the parent molecule.

The term "alkylamino" refers to a "substituted amino" of the formula (—$NR^h{}_2$), wherein $R^h$ is, independently, a hydrogen or an optionally substituted alkyl group as defined herein, and the nitrogen moiety is directly attached to the parent molecule.

The term "aryl" refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl" refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula (—$OR^i$), wherein $R^i$ is an optionally substituted aryl group as defined herein, and the oxygen moiety is directly attached to the parent molecule.

The term "arylamino," refers to a "substituted amino" of the formula (—$NR^h{}_2$), wherein $R^h$ is, independently, a hydrogen or an optionally substituted aryl group as defined herein, and the nitrogen moiety is directly attached to the parent molecule.

The term "arylthioxy" refers to a "substituted thiol" of the formula (—$SR^r$), wherein $R^r$ is an optionally substituted aryl group as defined herein, and the sulfur moiety is directly attached to the parent molecule.

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, the terms "heteroalkyl", "heteroalkenyl", "heteroalkynyl", and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" refers to an alkyl moiety, as defined herein, which contain one or more oxygen, sulfur, nitrogen, phosphorus, or silicon atoms, e.g., in place of carbon atoms.

The term "heteroalkenyl" refers to an alkenyl moiety, as defined herein, which contain one or more oxygen, sulfur, nitrogen, phosphorus, or silicon atoms, e.g., in place of carbon atoms.

The term "heteroalkynyl" refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—$NR^h{}_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula (—$SR^r$), wherein $R^r$ is an optionally substituted heteroalkyl group, as defined herein, and the sulfur moiety is directly attached to the parent molecule.

The term "heterocyclic," "heterocycles," or "heterocyclyl" refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl" refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene" refers to a divalent moiety formed by removing two hydrogen atoms from a heteroaryl compound, which is not a monovalent moiety, or by removing one hydrogen atom from a heteroaryl monovalent moiety.

The term "heteroarylamino" refers to a "substituted amino" of the ($-NR^h{}_2$), wherein $R^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula ($-OR^t$), wherein $R^t$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy" or "hydroxyl" refers to a group of the formula ($-OH$). A "substituted hydroxyl" refers to a group of the formula ($-OR^t$), wherein $R^t$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino" refers to a group of the formula ($=NR^r$), wherein $R^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to $=NH$ wherein $R^r$ is hydrogen.

The term "nitro" refers to a group of the formula ($-NO_2$).
The term "oxo" refers to a group of the formula ($=O$).

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group ($-OH$), with the exception of the first and last carbons, is asymmetric, making the carbon atom a stereocenter with two possible configurations (R or S). Because of this asymmetry, a number of isomers may exist for any given monosaccharide formula. The aldohexose d-glucose, for example, has the formula $C_6H_{12}O_6$, of which all but two of its six carbons atoms are stereogenic, making d-glucose one of the 16 (i.e., $2^4$) possible stereoisomers. The assignment of d or l is made according to the orientation of the asymmetric carbon furthest from the carbonyl group: in a standard Fischer projection if the hydroxyl group is on the right the molecule is a d sugar, otherwise it is an l sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, trehalose, and cellobiose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

A "monovalent radical" or "monovalent moiety" is a moiety formed by removing one hydrogen atom from a molecule. For example, a monovalent carbohydrate radical is a moiety formed by removing one hydrogen atom from a carbohydrate. A "divalent radical" or "divalent moiety" is a moiety formed by removing two hydrogen atoms from a molecule. For example, a divalent carbohydrate radical is a moiety formed by removing two hydrogen atoms from a carbohydrate. A divalent peptide radical is a moiety formed by removing two hydrogen atoms from a peptide. The atom from which a hydrogen atom is removed is a point of attachment.

A "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

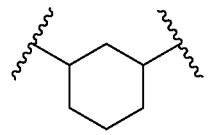

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

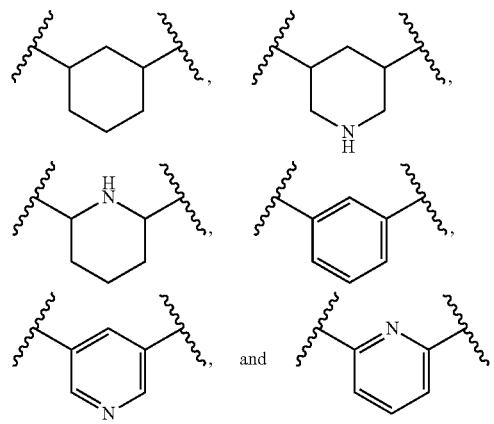

are all examples of a hydrocarbon chain. Hydrocarbon chains also include a divalent carbohydrate radical (wherein one or two oxygen atoms at the points of attachment may be present or absent), such as a divalent glucose radical (e.g.,

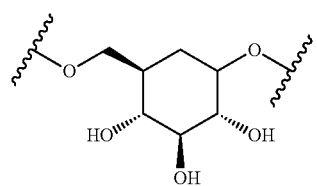 [SMILES: *OC[C@H]1CC(O*)[C@H](O)[C@@H](O)[C@@H]1O]

(both two oxygen atoms at the points of attachment are present) and

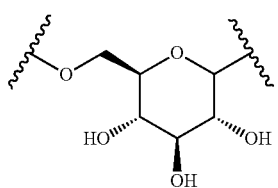 [SMILES: *OC[C@H]1OC(*)[C@H](O)[C@@H](O)[C@@H]1O]

(only one of the two oxygen atom at the points of attachment is present)). In contrast, in certain embodiments

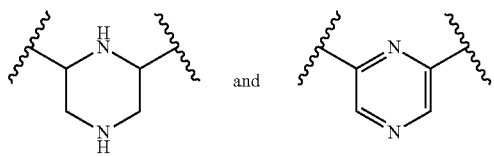 [SMILES: *C1CNCC(*)N1 ; *c1cncc(*)n1]

are not within the scope of the hydrocarbon chains described herein.

A "protecting group" is well known in the art and include those described in detail in Greene's Protective Groups in Organic Synthesis, P. G. M. Wuts and T. W. Greene, 4th edition, Wiley-Interscience, 2006, the entirety of which is incorporated herein by reference. Suitable "amino-protecting groups" (also referred to as "nitrogen protecting groups") include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "hydroxyl protecting group" (also referred to as an "oxygen protecting group") is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., Ca(OH)$_2$), magnesium (by using, e.g., Mg(OH)$_2$ and magnesium acetate), zinc, (by using, e.g., Zn(OH)$_2$ and zinc acetate), and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, ketene-ynol forms, enamine-enamine forms, and pyridione-hydroxypyridine forms.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "intracellular conditions" refers to conditions of the internal milieu that occur in a subject (e.g., a human) naturally, as opposed to artificial laboratory conditions. In certain embodiments, intracellular conditions include a temperature range of about 20 to about 40° C. (e.g., about 37° C.), pressure of about 1 atmosphere, pH of about 6 to about 8 (e.g., about 7), glucose concentration of about 1 to about 20 mM, atmospheric oxygen concentration, and earth gravity. In certain embodiments, intracellular conditions are conditions that occur in a bacterium (e.g., a bacterium described herein).

The term "stable under intracellular conditions" refers to a compound or a moiety of a compound (e.g., linker L of a compound of Formula (I)) showing a long half-life under intracellular conditions. The concentration of the compound or the moiety at the inception of the half-life measurement is a concentration effective for the intended use of the compound. In certain embodiments, the concentration of the compound or the moiety at the inception of the half-life measurement is the half maximal inhibitory concentration (IC$_{50}$) of the compound in inhibiting the growth of a bacterium (e.g., a bacterium described herein). In certain embodiments, a long half-life is at least about 20 min, 1 hour, 3 hours, 6 hours, at least about 12 hours, or at least about 24 hours.

The term "hydrophobic" or "non-polar" refers to the ability of a compound to dissolve, or the ability of a moiety of a compound to assist the compound in dissolving in fats, oils, lipids, and/or non-polar solvents (e.g., hexane or toluene). Hydrophobic moieties include, but are not limited to, substituted or unsubstituted, branched or unbranched alkyl or alkylene groups having 1 to 50 carbon atoms. In certain embodiments, the hydrophobic moiety is an alkyl or alkylene group including at least 1, at least 6, at least 12, at least 18, at least 24, at least 36, or at least 50 carbon atoms. In certain embodiments, the hydrophobic moiety is unsubstituted alkyl or alkylene. In certain embodiments, the hydrophobic moiety is unsubstituted alkyl or alkylene. In certain embodiments, the hydrophobic moiety is unsubstituted C$_{1-24}$ alkyl or alkylene.

The term "hydrophilic" or "polar" refers to the ability of a compound to dissolve, or the ability of a moiety of a compound to assist the compound in dissolving in water. A hydrophilic compound or moiety typically includes one or more heteroatoms (e.g., atoms that are not carbon or hydrogen). In certain embodiments, the water solubility of a hydrophilic compound is at least about 1 mg/ml, at least about 3 mg/ml, or at least about 10 mg/ml at 25° C. and 1 atmosphere. A hydrophilic compound or moiety is not hydrophobic.

The term "conjugate" refers to a compound formed by covalently attaching directly or indirectly (e.g., through a divalent linker) one compound to another compound. In certain embodiments, a conjugate (e.g., an enterobactin-carrier protein conjugate, or a salmochelin-carrier protein conjugate) is a compound of Formula (I), or a salt, hydrate, solvate, polymorph, co-crystal, tautomer, or isotopically labeled derivative thereof.

The term "PEG" refers to a -poly(ethylene glycol)-divalent moiety. The term "$PEG_x$" refers to a -(poly(ethylene glycol))$_x$-divalent moiety, wherein x is an integer from 1 to 10, inclusive.

The term "subject" refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep, or chicken).

The terms "administer," "administering," or "administration" refers to injecting, implanting, absorbing, ingesting, or inhaling a compound described herein, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of the present invention or a pharmaceutical composition thereof refers to an amount sufficient to elicit the desired biological response, e.g., treating the condition or inducing an immune response against the conjugates described herein. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutically and prophylactically effective amounts.

A "therapeutically effective amount" of a compound of the present invention or a pharmaceutical composition thereof is an amount sufficient to provide a therapeutic benefit in the treatment of a disease or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound of the present invention is an amount sufficient to prevent a disease or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

Compounds

In one aspect, the present invention provides a family of enterobactin-carrier protein conjugates. Enterobactin may be derivatized at the 4-, 5-, or 6-position of the catecholate moiety. For example, enterobactin may be derivatized at the 5-position of the catecholate moiety, which provides a point for site-specific modification without compromising the Fe(III)-binding groups or the macrolactone.

In certain embodiments, the compounds of Formula (I) includes salts and stereoisomers thereof. In certain embodiments, the compounds of Formula (I) includes salts thereof. In certain embodiments, the compounds of Formula (I) includes pharmaceutically acceptable salts thereof. In certain embodiments, a compound of Formula (I) is a mixture of stereoisomers. In certain embodiments, a compounds of Formula (I) is a racemic mixture of stereoisomers. In certain embodiments, a compounds of Formula (I) is a substantially pure stereoisomer.

A compound of Formula (I) includes one or more enterobactin moiety Ent; one or more linker moieties L; and one or more carrier protein moieties CP (preferably one). In certain embodiments, L is stable under intracellular conditions. In certain embodiments, the half-life of at least one instance of L under physiological conditions is at least about 6 hours, at least about 12 hours, at least about 1 day, at least about 2 days, at least about 3 days, at least about 5 days, or at least about 1 week. In certain embodiments, at least one instance of L is hydrophilic. In certain embodiments, at least one instance of L is hydrophobic. In certain embodiments, the molecular weight of at least one instance of L is less than about 600 Da, less than about 500 Da, less than about 400 Da, less than about 300 Da, or less than about 200 Da. In certain embodiments, the molecular weight of at least one instance of L is at least about 600 Da, at least about 500 Da, at least about 400 Da, at least about 300 Da, or at least about 200 Da. In certain embodiments, at least one instance of L consists of less than about 150 atoms, less than about 100 atoms, less than about 70 atoms, less than about 50 atoms, or less than about 30 atoms. In certain embodiments, at least one instance of L consists of at least about 150 atoms, at least about 100 atoms, at least about 70 atoms, at least about 50 atoms, or at least about 30 atoms. In certain embodiments, at least one instance of L consists of less than about 10, less than about 8, less than about 6, or less than about 4 unsaturated bonds. In certain embodiments, at least one instance of L consists of 0, 1, or 2 unsaturated bonds. In certain embodiments, at least one instance of L consists of at least about 10, at least about 8, at least about 6, or at least about 4 unsaturated bonds. In certain embodiments, the distance between the two points of attachment of at least one instance of L is less than about 15 Å, less than about 20 Å, less than about 30 Å, less than about 40 Å, less than about 50 Å, less than about 70 Å, or less than about 100 Å, when L is under the minimum-energy conformation. In certain embodiments, the distance between the two points of attachment of at least one instance of L is at least about 15 Å, at least about 20 Å, at least about 30 Å, at least about 40 Å, at least about 50 Å, at least about 70 Å, or at least about 100 Å, when L is under the minimum-energy conformation. Combinations of the ranges described herein (e.g., the molecular weight of at least one instance of L being at least about 200 Da and less than about 1.4 kDa) are also with the scope of the present invention.

In certain embodiments, each instance of L is independently a bond or a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene; and each instance of R$^L$ is independently hydrogen, substituted or unsubstituted $C_{1-6}$ alkyl, or a nitrogen protecting group.

In certain embodiments, at least one instance of L is a bond. In certain embodiments, at least one instance of L is a divalent linker. Either one of the two points of attachment of L may be attached to a phenyl ring of a conjugate described herein. In certain embodiments, at least one instance of L is a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{1-100}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{6-36}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, at least one instance of L is a substituted or unsubstituted $C_{12-36}$ hydrocarbon chain, optionally wherein one or more carbon units of the hydrocarbon chain are independently replaced with —O—, —S—, —NR$^L$—, —S(=O)—, —S(=O)$_2$—, or substituted or unsubstituted heteroarylene. In certain embodiments, 1 to 10 carbon units of at least one instance of L are independently replaced with —O—, —S—, —NR$^L$—, —S(=O)—, —S(=O)$_2$—, or substituted or unsubstituted heteroarylene. In certain embodiments, 3 to 8 carbon units of at least one instance of L are independently replaced with —O—, —S—, —NR$^L$—, —S(=O)—, —S(=O)$_2$—, or substituted or unsubstituted heteroarylene.

In certain embodiments, at least one instance of L is a divalent peptide radical. In certain embodiments, at least one instance of L is a divalent peptide radical consisting of between 2 and 80 amino acid residues, inclusive. In certain embodiments, at least one instance of L is a divalent peptide radical consisting of between 2 and 6 amino acid residues, inclusive. In certain embodiments, at least one instance of L is a divalent peptide radical consisting of between 7 and 15 amino acid residues, inclusive. In certain embodiments, at least one instance of L is a divalent peptide radical consisting of between 16 and 80 amino acid residues, inclusive.

In certain embodiments, two carbon units of at least one instance of L are independently replaced with substituted or unsubstituted heteroarylene. In certain embodiments, one carbon unit of at least one instance of L is replaced with substituted or unsubstituted heteroarylene. In certain embodiments, at least one instance of the substituted or unsubstituted heteroarylene of at least one instance of L is substituted or unsubstituted, 5- to 6-membered, monocyclic heteroaryl, wherein one, two, three, or four atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 5-membered, monocyclic heteroaryl, wherein one atom in the heteroaryl ring system is nitrogen, oxygen, or sulfur. In certain embodiments, at least one instance of the substituted or unsubstituted heteroarylene of at least one instance of L is substituted or unsubstituted, 5-membered, monocyclic heteroaryl, wherein two atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 5-membered, monocyclic heteroaryl, wherein three atoms in the heteroaryl ring system are independently selected from the group consisting of nitrogen, oxygen, and sulfur. In certain embodiments, at least one instance of the substituted or unsubstituted heteroarylene of at least one instance of L is of the formula:

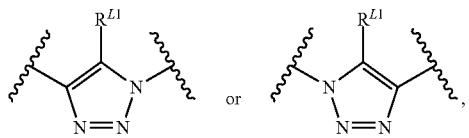

wherein $R^{L1}$ is hydrogen, halogen, unsubstituted $C_{1-6}$ alkyl, or $C_{1-6}$ alkyl substituted with at least one halogen. In certain embodiments, at least one instance of the substituted or unsubstituted heteroarylene of at least one instance of L is of the formula:

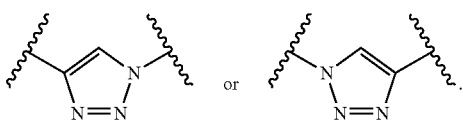 [SMILES: *c1cn(*)nn1 ; *c1cn(*)nn1] or

In certain embodiments, at least one instance of the substituted or unsubstituted heteroarylene of at least one instance of L is substituted or unsubstituted, 5-membered, monocyclic heteroaryl, wherein four atoms in the heteroaryl ring system are independently selected from the group consisting of nitrogen, oxygen, and sulfur. In certain embodiments, at least one instance of the substituted or unsubstituted heteroarylene of at least one instance of L is substituted or unsubstituted, 6-membered, monocyclic heteroaryl, wherein one atom in the heteroaryl ring system is nitrogen. In certain embodiments, at least one instance of the substituted or unsubstituted heteroarylene of at least one instance of L is substituted or unsubstituted, 6-membered, monocyclic heteroaryl, wherein two atoms in the heteroaryl ring system are nitrogen. In certain embodiments, at least one instance of the substituted or unsubstituted heteroarylene of at least one instance of L is substituted or unsubstituted, 6-membered, monocyclic heteroaryl, wherein three atoms in the heteroaryl ring system are nitrogen.

In certain embodiments, at least one instance of L is a divalent hydrocarbon radical. In certain embodiments, at least one instance of L is a divalent monosaccharide radical. In certain embodiments, at least one instance of L is a divalent hexose radical. In certain embodiments, at least one instance of L is a divalent aldohexose radical. In certain embodiments, at least one instance of L is a divalent glucose radical (e.g., a divalent radical of α-D-, β-D-, α-L-, or β-L-glucose). In certain embodiments, at least one instance of L is a divalent dextrose radical. In certain embodiments, at least one instance of L is a divalent glucopyranose radical. In certain embodiments, at least one instance of L is of the formula:

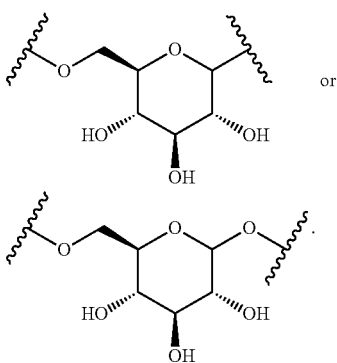

In certain embodiments, at least one instance of L is of the formula:

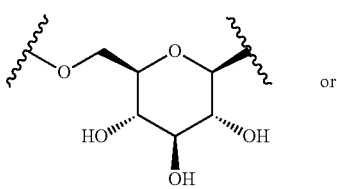

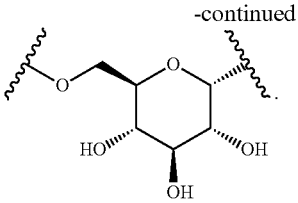

In certain embodiments, at least one instance of L is of the formula:

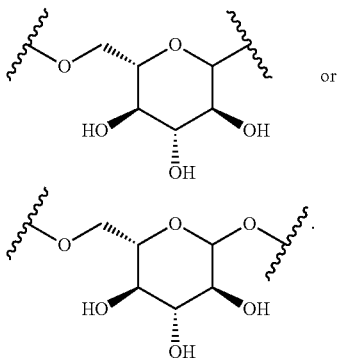

In certain embodiments, at least one instance of L is a divalent glucofuranose radical. In certain embodiments, at least one instance of L is a divalent radical of mannose, galactose, allose, altrose, talose, gulose, or idose. In certain embodiments, at least one instance of L is a divalent ketohexose radical (e.g., a divalent radical of fructose, psicose, sorbose, or tagatose). In certain embodiments, at least one instance of L is a divalent aldopentose radical (e.g., a divalent radical of ribose, arabinose, xylose, or lyxose) or a divalent ketopentose radical (e.g., a divalent radical of ribulose, arabulose, xylulose, or lyxulose). In certain embodiments, at least one instance of L is a divalent disaccharide radical or divalent polysaccharide radical.

In certain embodiments, at least one instance of L is a combination of two or more divalent radicals described herein, wherein any two divalent radicals are independently the same or different.

In certain embodiments, no instance of L comprises a divalent peptide radical (e.g., a divalent radical of a peptide consisting of between 7 and 15 amino acid residues, inclusive, or a divalent radical of a peptide consisting of 81 or more amino acid residues). In certain embodiments, no instance of L comprises a divalent radical formed by removing two hydrogen atoms from a peptide of the sequence: SSSGSGS, SATSSSGSGS, GYNSATSSSGSGS, SSGYNSATSSSGSGS, SATSSSGSGG, SATSSSGSGA, SATSSSGSGT, SASSSAGGGS, SSTSSAVSGS, or SASSSAGSGS. In certain embodiments, no instance of L comprises a divalent radical formed by removing two hydrogen atoms from a peptide of the sequence GETDPNTQLLNDL-GNNMAWGAALGAPGGLGSAALGAAGGALQT-VGQGLIDHGPV NVPIPVLIGPSWNGSSSGYN-SATSSSGSGS. In certain embodiments, no instance of L comprises both a divalent peptide radical and a divalent carbohydrate radical (e.g., a divalent glucose radical). In certain embodiments, no instance of L is -(divalent peptide radical)-(divalent carbohydrate radical)-. In certain embodiments, no instance of L is -(divalent peptide radical)-(divalent glucose radical)-. In certain embodiments, no instance of L is of the formula:

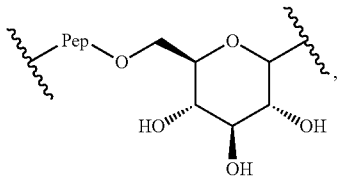

wherein -Pep- is a divalent peptide radical. In certain embodiments, the carbonyl moiety of the C-terminus of -Pep- is attached to the oxygen atom at $C_6$ of the glucose moiety, and the nitrogen atom of the N-terminus of -Pep- is attached to X. In certain embodiments, -Pep- is a divalent radical of a peptide of the sequence: SSSGSGS, SATSSSGSGS, GYNSATSSSGSGS, SSGYN-SATSSSGSGS, SATSSSGSGG, SATSSSGSGA, SATSSSGSGT, SASSSAGGGS, SSTSSAVSGS, or SASSSAGSGS. In certain embodiments, -Pep- is a divalent radical of a peptide of the sequence: GETDPNTQLLNDLGN-NMAWGAALGAPGGLGSAALGAAGGALQTVGQGL-IDHGPV NVPIPVLIGPSWNGSSSGYNSATSSSGSGS.

In certain embodiments, at least one instance of $R^L$ is hydrogen. In certain embodiments, at least one instance of $R^L$ is substituted alkyl. In certain embodiments, at least one instance of $R^L$ is unsubstituted alkyl. In certain embodiments, at least one instance of $R^L$ is $C_{1-12}$ alkyl. In certain embodiments, at least one instance of $R^L$ is $C_{1-6}$ alkyl. In certain embodiments, at least one instance of $R^L$ is unsubstituted methyl. In certain embodiments, at least one instance of $R^L$ is substituted methyl. In certain embodiments, at least one instance of $R^L$ is —CH$_2$F, —CHF$_2$, or —CF$_3$. In certain embodiments, at least one instance of $R^L$ is Bn. In certain embodiments, at least one instance of $R^L$ is ethyl, propyl, butyl, pentyl, or hexyl. In certain embodiments, at least one instance of $R^L$ is a nitrogen protecting group. In certain embodiments, at least one instance of $R^L$ is Bn, Boc, Cbz, Fmoc, trifluoroacetyl, triphenylmethyl, acetyl, or Ts. In certain embodiments, at least one instance of $R^L$ is hydrogen, unsubstituted $C_{1-6}$ alkyl, and $C_{1-6}$ alkyl substituted with one or more substituents independently selected from the group consisting of halogen and —O(unsubstituted $C_{1-6}$ alkyl).

In the divalent linker L, each instance of the carbon units of the $C_{1-100}$ hydrocarbon chain and each instance of the heteroarylene may be independently substituted. In certain embodiments, at least one instance of the carbon units of the $C_{1-100}$ hydrocarbon chain or at least one instance of the heteroarylene is substituted with hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, =O, —OR$^{L1}$, —N(R$^{L1}$)$_2$, —SR$^{L1}$, —CN, —SCN, —C(=NR$^{L1}$)R$^{L1}$, —C(=NR$^{L1}$)OR$^{L1}$, —C(=NR$^{L1}$)N(R$^{L1}$)$_2$, —C(=O)R$^{L1}$, —C(=O)OR$^{L1}$, —C(=O)N(R$^{L1}$)$_2$, —S(=O)R$^{L1}$, —S(=O)OR$^{L1}$, —S(=O)N(R$^{L1}$)$_2$, —S(=O)$_2$R$^{L1}$, —S(=O)$_2$OR$^{L1}$, —S(=O)$_2$N(R$^{L1}$)$_2$, —NO$_2$, —NR$^{L1}$C(=O)R$^{L1}$, —NR$^{L1}$C(=O)OR$^{L1}$, —NR$^{L1}$C(=O)N(R$^{L1}$)$_2$, —NR$^{L1}$S(=O)R$^{L1}$, —NR$^{L1}$S(=O)OR$^{L1}$, —NR$^{L1}$S(=O)N(R$^{L1}$)$_2$, —NR$^{L1}$S(=O)$_2$R$^{L1}$, —NR$^{L1}$S(=O)$_2$OR$^{L1}$, —NR$^{L1}$S(=O)$_2$N(R$^{L1}$)$_2$, —OC(=O)R$^{L1}$, —OC(=O)OR$^{L1}$, —OC(=O)N(R$^{L1}$)$_2$, —OS(=O)R$^{L1}$, —OS(=O)OR$^{L1}$, —OS(=O)N(R$^{L1}$)$_2$, —OS(=O)$_2$R$^{L1}$, —OS(=O)$_2$OR$^{L1}$, —OS(=O)$_2$N(R$^{L1}$)$_2$, wherein each occurrence of R$^{L1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{L1}$ groups are joined to form an substituted or unsubstituted heterocyclic ring, provided that no instance of the heteroarylene is substituted with =O. In certain embodiments, at least one instance of the carbon units of the $C_{1-100}$ hydrocarbon chain is substituted with halogen, =O, or substituted or unsubstituted alkyl. In certain embodiments, at least one instance of the carbon units of the $C_{1-100}$ hydrocarbon chain is substituted with halogen, =O, unsubstituted $C_{1-6}$ alkyl, or $C_{1-6}$ alkyl substituted with at least one halogen. In certain embodiments, at least one instance of the heteroarylene is substituted with halogen or substituted or unsubstituted alkyl. In certain embodiments, at least one instance of the heteroarylene is substituted with halogen, unsubstituted $C_{1-6}$ alkyl, or $C_{1-6}$ alkyl substituted with at least one halogen. In certain embodiments, no instance of the carbon units of the $C_{1-100}$ hydrocarbon chain and no instance of the heteroarylene is substituted with substituted or unsubstituted alkenyl or substituted or unsubstituted alkynyl. In certain embodiments, at least one instance of L is of the formula:

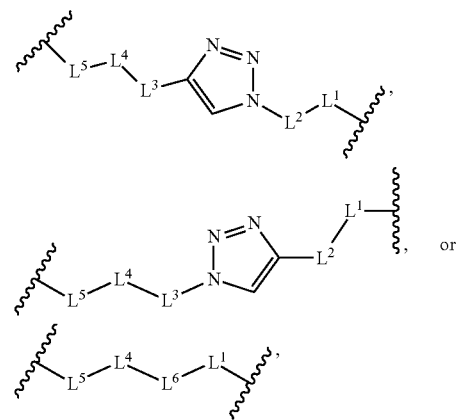

wherein: $L^1$ and $L^4$ are independently —NR$^L$C(=O)— or —C(=O)NR$^L$—; $L^2$ and $L^3$ are independently unsubstituted $C_{1-50}$ alkylene or $C_{1-50}$ alkylene substituted with at least one halogen, optionally wherein one to six carbon units of the $C_{1-50}$ alkylene are replaced with —O—; $L^5$ is a bond, unsubstituted $C_{1-6}$ alkylene, or $C_{1-6}$ alkylene substituted with at least one halogen, optionally wherein one or two carbon units of the $C_{1-6}$ alkylene are replaced with —O—; and $L^6$ is unsubstituted $C_{2-90}$ alkylene, or $C_{2-90}$ alkylene substituted with at least one halogen, optionally wherein one to eight carbon units of the $C_{2-90}$ alkylene are replaced with —O—. In certain embodiments, at least one instance of L is of the formula:

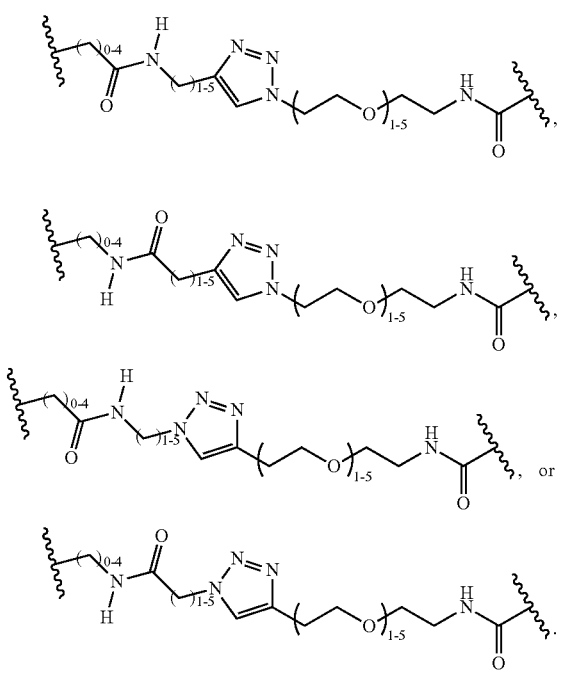

In certain embodiments, at least one instance of L is of the formula:

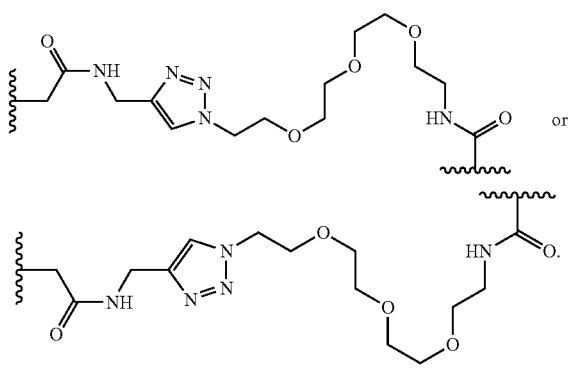

In certain embodiments, at least one instance of L is of the formula:

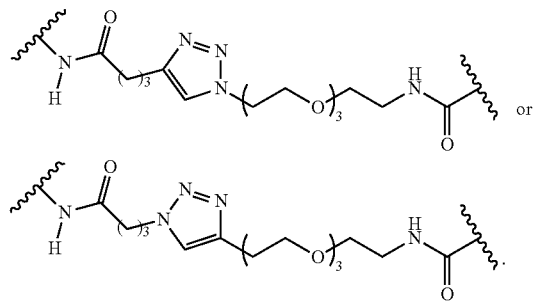

In certain embodiments, at least one instance of L is of the formula:

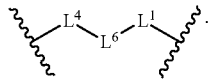

In certain embodiments, at least one instance of L is —NHC(=O)—(CH₂)₂₋₈—NHC(=O)— or —C(=O)NH—(CH₂)₂₋₈—C(=O)NH—. In certain embodiments, at least one instance of L is —NHC(=O)—(CH₂)₅—NHC(=O)— or —C(=O)NH—(CH₂)₅—C(=O)NH—. In certain embodiments, at least one instance of L is of the formula:

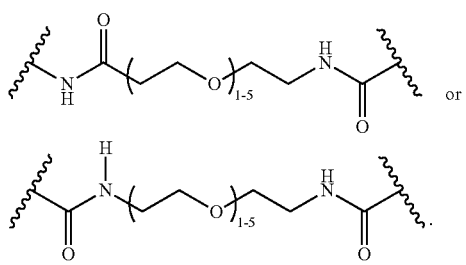

In certain embodiments, at least one instance of L is of the formula:

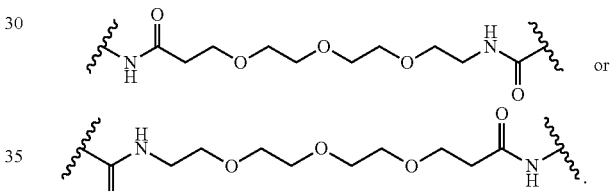

A conjugate described herein may be purified by semi-preparative HPLC and characterized by analytical HPLC, mass spectrometry, and optical absorption spectroscopy.

Compositions, Kits, and Administration

The present invention provides compositions comprising a compound of Formula (I) (e.g., a compound of Formula (I), or a salt, hydrate, solvate, polymorph, co-crystal, tautomer, stereoisomer, or isotopically labeled derivative thereof), and optionally an excipient. In certain embodiments, a composition of the invention comprises a compound of Formula (I), or a salt or stereoisomer thereof, and optionally an excipient. In certain embodiments, a composition of the invention comprises a compound of Formula (I), or a salt thereof, and an excipient. In certain embodiments, a composition of the invention is a pharmaceutical composition. In certain embodiments, a pharmaceutical composition of the invention comprises a compound of Formula (I), or a pharmaceutically acceptable salt, hydrate, solvate, polymorph, co-crystal, tautomer, stereoisomer, or isotopically labeled derivative thereof, and optionally a pharmaceutically acceptable excipient. In certain embodiments, a pharmaceutical composition of the invention comprises a compound of Formula (I), or a pharmaceutically acceptable salt or stereoisomer thereof, and optionally a pharmaceutically acceptable excipient. In certain embodiments, a pharmaceutical composition of the invention comprises a compound of Formula (I), or a pharmaceutically acceptable salt thereof, and a pharmaceutically acceptable excipient.

The present invention also provides compositions comprising an antibody that selectively binds enterobactin or salmochelin (e.g., raised against a compound of Formula (I)), and optionally an excipient. In certain embodiments, a composition of the invention is a pharmaceutical composition. In certain embodiments, a pharmaceutical composition of the invention comprises an antibody that selectively binds enterobactin or salmochelin, or an analog thereof, and optionally a pharmaceutically acceptable excipient.

In certain embodiments, the compound of Formula (I) or an effective amount of an antibody that selectively binds enterobactin or salmochelin, or an analog thereof, is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a bacterial infection (e.g., a bacterial infection described herein). In certain embodiments, the effective amount is an amount effective for preventing a bacterial infection. In certain embodiments, the effective amount is an amount effective for treating an infection caused by a Gram-negative bacterium (e.g., a Gram-negative bacterium described herein). In certain embodiments, the effective amount is an amount effective for preventing an infection caused by a Gram-negative bacterium. In certain embodiments, the effective amount is an amount effective for treating inflammatory bowel disease (IBD). In certain embodiments, the effective amount is an amount effective for preventing IBD.

An effective amount of a compound or an effective amount of an antibody that selectively binds enterobactin or salmochelin may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of a compound of Formula (I) or an effective amount of an antibody that selectively binds enterobactin or salmochelin, or an analog thereof, may be an amount effective for inhibiting the growth and/or reproduction of a bacterium or killing a bacterium. In certain embodiments, the effective amount is an amount effective for inhibiting the growth or reproduction of a bacterium or killing a bacterium by at least about 10%, at least about 20%, at least about 30%, at least about 40%, at least about 50%, at least about 60%, at least about 70%, at least about 80%, or at least about 90%. In certain embodiments, the growth or reproduction of a bacterium is inhibited by a percentage described herein by an effective amount of a compound of Formula (I) or an effective amount of an antibody that selectively binds enterobactin or salmochelin, or an analog thereof.

Pharmaceutical compositions described herein can be prepared by any method known in the art of pharmacology. In general, such preparatory methods include the steps of bringing the compound of Formula (I) (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound of this invention may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes of administration of the compounds and compositions disclosed herein are inhalation and intranasal administration, subcutaneous administration, mucosal administration, and interdermal administration. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition of the invention is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional agents (e.g., pharmaceutical agents (e.g., therapeutically and/or prophylactically active agents) or diagnostic agents (e.g., imaging agents). The compounds or compositions can be administered in combination with additional agents that improve their activity (e.g., potency and/or efficacy) in treating a bacterial infection and/or IBD in a subject in need thereof, in preventing a bacterial infection and/or IBD in a subject in need thereof, in inhibiting the growth and/or reproduction of a bacterium, and/or in killing a bacterium, bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, an inventive composition including a compound of Formula (I) and an additional agent shows a synergistic effect that is absent in a composition including one of the compound and the additional agent, but not both.

The compound or composition can be administered concurrently with, prior to, or subsequent to one or more additional agents, which may be useful as, e.g., combination therapies. Additional agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional agent is a pharmaceutical agent useful in treating a bacterial infection and/or IBD, in preventing a bacterial infection and/or IBD in a subject in need thereof, in inhibiting the growth and/or reproduction of a bacterium, and/or in killing a bacterium. Each additional agent may be employed (e.g., administered) at a dose and/or on a time schedule determined for that agent. The additional agents may also be employed together with each other and/or with the compound or composition described herein in a single dose or employed separately in different doses. The particular combination to employ in a regimen will take into account compatibility of the compound of Formula (I) with the additional agent(s) and/or the desired effect (e.g., therapeutic and/or prophylactic effect) to be achieved. In general, it is expected that the additional agent(s) utilized in combination be utilized at levels that do not exceed the levels at which they are utilized individually. In some embodiments, the levels utilized in combination will be lower than those utilized individually.

In certain embodiments, the additional agent is a pharmaceutical agent. Additional pharmaceutical agents include, but are not limited to, adjuvants (immunological adjuvants), anti-bacterial agents, anti-fungal agents, anti-viral agents, anti-proliferative agents, anti-cancer agents, anti-angiogenesis agents, anti-inflammatory agents, immunosuppressants, anti-diabetic agents, anti-allergic agents, pain-relieving agents, and iron chelators. In certain embodiments, the additional pharmaceutical agent is an adjuvant, such as alum; MF59; R848; cholera toxin; squalene; phosphate adjuvants; tetrachlorodecaoxide; monophosphoryl lipid A (MPL, SmithKline Beecham); saponins including QS21 (SmithKline Beecham); immunostimulatory oligonucleotides (e.g., CpG immunostimulatory oligonucleotides first described by Kreig et al., Nature 374:546-9, 1995); incomplete Freund's adjuvant; complete Freund's adjuvant; montanide; vitamin E and various water-in-oil emulsions prepared from biodegradable oils such as squalene and/or tocopherol; Quil A; Ribi Detox; CRL-1005; or L-121. In certain embodiments, the additional pharmaceutical agent is an antibiotic. In certain embodiments, the additional pharmaceutical agent is an antibiotic effective against a Gram-negative bacterium. In certain embodiments, the additional pharmaceutical agent is an antibiotic effective against a Gram-positive bacterium. In certain embodiments, the additional pharmaceutical agent is a β-lactam antibiotic. In certain embodiments, the additional pharmaceutical agent is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g, pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the compounds of Formula (I), or compositions thereof, can be administered in combination with an anti-cancer therapy including, but not limited to, surgery, radiation therapy, and chemotherapy. In certain embodiments, the additional agent is an iron chelator (e.g., 2,2'-dipyridyl, desferrioxamine (DFO, Desferal®), deferasirox (Exjade®), deferiprone (L1, Ferriprox®), Feralex-G, CaNa$_3$DTPA, dexrazoxane, a phosphorothioate-oligonucleotide, desferrithiocin, desazadesferrithiocin, or a derivative thereof). In certain embodiments, the additional agent is a Fe(III) chelator. In certain embodiments, the additional agent is a Fe(II) chelator. In certain embodiments, the additional agent is an antifungal agent, such as amphotericin B, fluconazole, itraconazole, ketoconazole, potassium iodide, flucytosine, and the like.

Also encompassed by the invention are kits (e.g., pharmaceutical packs). The kits provided may comprise a compound of Formula (I) or composition (e.g., pharmaceutical or diagnostic composition) and a container (e.g., a vial, ampule, bottle, syringe, and/or dispenser package, or other suitable container). The kits provided may comprise antibodies that selectively bind an enterobactin or a salmochelin or composition (e.g., pharmaceutical or diagnostic composition) and a container (e.g., a vial, ampule, bottle, syringe, and/or dispenser package, or other suitable container). In some embodiments, provided kits may optionally further include a second container comprising an excipient (e.g., pharmaceutically acceptable excipient) for dilution or suspension of an inventive pharmaceutical composition or compound. In some embodiments, the compound of Formula (I) or composition provided in the first container and the second container are combined to form one unit dosage form.

Thus, in one aspect, the present invention provides kits including a first container comprising a compound of Formula (I), or a salt, solvate, hydrate, polymorph, co-crystal, tautomer, stereoisomer, or isotopically labeled derivative thereof, or a composition thereof. In certain embodiments, a provided kit includes a first container comprising a compound of Formula (I), or a salt or stereoisomer thereof, or a composition thereof. In certain embodiments, a provide kit includes a first container comprising a compound of Formula (I), or a pharmaceutically acceptable salt thereof, or a pharmaceutical composition thereof.

In another aspect, the present invention provides kits including a first container comprising antibodies produced using the compound of Formula (I), i.e., antibodies that selectively bind an enterobactin or a salmochelin.

In certain embodiments, the kits are useful in treating and/or preventing a bacterial infection (e.g., a bacterial infection described herein) in a subject in need thereof. In certain embodiments, the bacterial infection is an infection caused by a Gram-negative bacterium. In certain embodiments, the kits are useful in inhibiting the growth and/or reproduction of a bacterium (e.g., a Gram-negative bacterium). In certain embodiments, the kits are useful in killing a bacterium (e.g., a Gram-negative bacterium). In certain embodiments, the kits are useful in treating and/or preventing IBD. In certain embodiments, the kits further include instructions for using the kit (e.g., for administering to a subject in need of treatment and/or prevention of a bacterial infection and/or IBD a compound of Formula (I), or a composition thereof). The kits may also include information as required by a regulatory agency such as the U.S. Food and Drug Administration (FDA). In certain embodiments, the information included in the kits is prescribing information. In certain embodiments, the kits and instructions provide for treating and/or preventing a bacterial infection in a subject in need thereof. In certain embodiments, the kits and instructions provide for treating and/or preventing IBD in a subject in need thereof. In certain embodiments, the kits and instructions provide for inhibiting the growth and/or reproduction of a bacterium. In certain embodiments, the kits and instructions provide for killing a bacterium. The kit of the invention may include one or more additional agents described herein as a separate composition.

Methods of Use

Another aspect of the present invention relates to methods of using the compounds of Formula (I), which are enterobactin-carrier protein conjugates, and compositions thereof, in pharmaceutical and non-pharmaceutical applications.

Enterobactin (Ent, FIG. 1) is a canonical siderophore biosynthesized by Gram-negative species of *Enterobacteriaceae* that include *Escherichia coli* (*E. coli*), *Salmonella*, and *Klebsiella* (Raymond et al. Proc. Natl. Acad. Sci. U.S.A 2003, 100, 3584-3588). Decades of exploration pertaining to enterobactin biosynthesis and coordination chemistry, in addition to investigations of the proteins involved in its cellular transport and processing, provide a detailed molecular and physiological understanding of how this chelate contributes to bacterial iron homeostasis and colonization (Raymond et al. Proc. Natl. Acad. Sci. U.S.A 2003, 100, 3584-3588). The enterobactin synthetase is comprised of four proteins, EntBDEF, and is responsible for the production of enterobactin from L-serine and 2,3-dihydroxybenzoic acid (DHB) (Crosa et al. Microbiol. Mol. Biol. Rev. 2002, 66, 223-249). Following biosynthesis, Ent is exported into the extracellular space where it scavenges Fe(III). Enterobactin coordinates Fe(III) by its three catecholate groups with $K_a \sim 10^{49}$ $M^{-1}$. (Loomis et al. Inorg. Chem. 1991, 30, 906-911). Several pathogenic Gram-negative species harbor gene clusters (e.g., iroA, MccE492) responsible for post-assembly line modifications of the enterobactin scaffold to provide the salmochelins (Lin et al. J. Am. Chem. Soc. 2005, 127, 11075-11084; Bäumler et al. J. Bacteriol. 1998, 180, 1446-1453; Lagos et al. Mol. Microbiol. 2001, 42, 229-243; Nolan et al. J. Am. Chem. Soc. 2007, 129, 14336-14347; Fischbach et al. Proc. Natl. Acad. Sci. U.S.A 2005, 102, 571-576).

Figure 1:
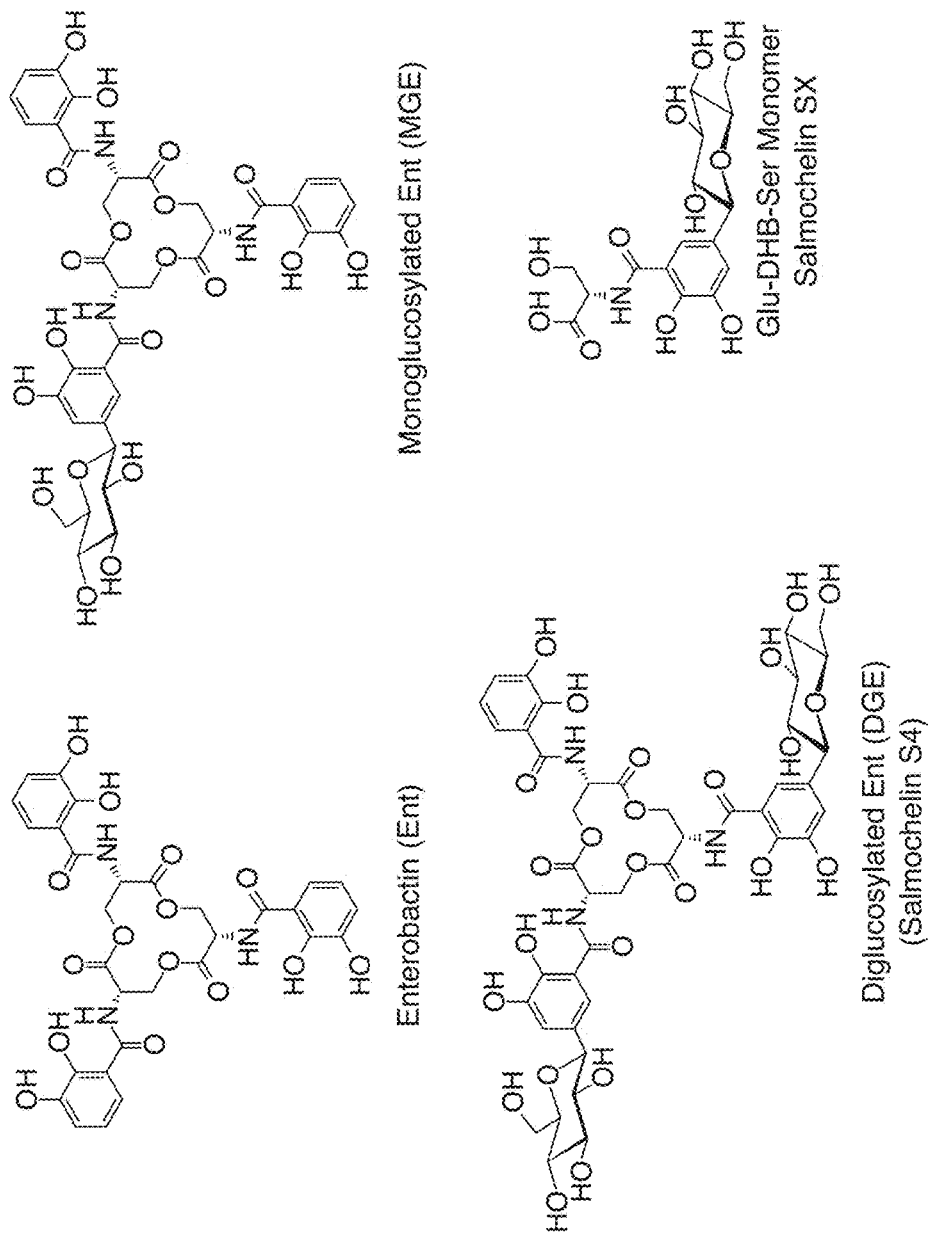
FIG. 1 shows chemical structures of enterobactin and salmochelins.
Figure 1:
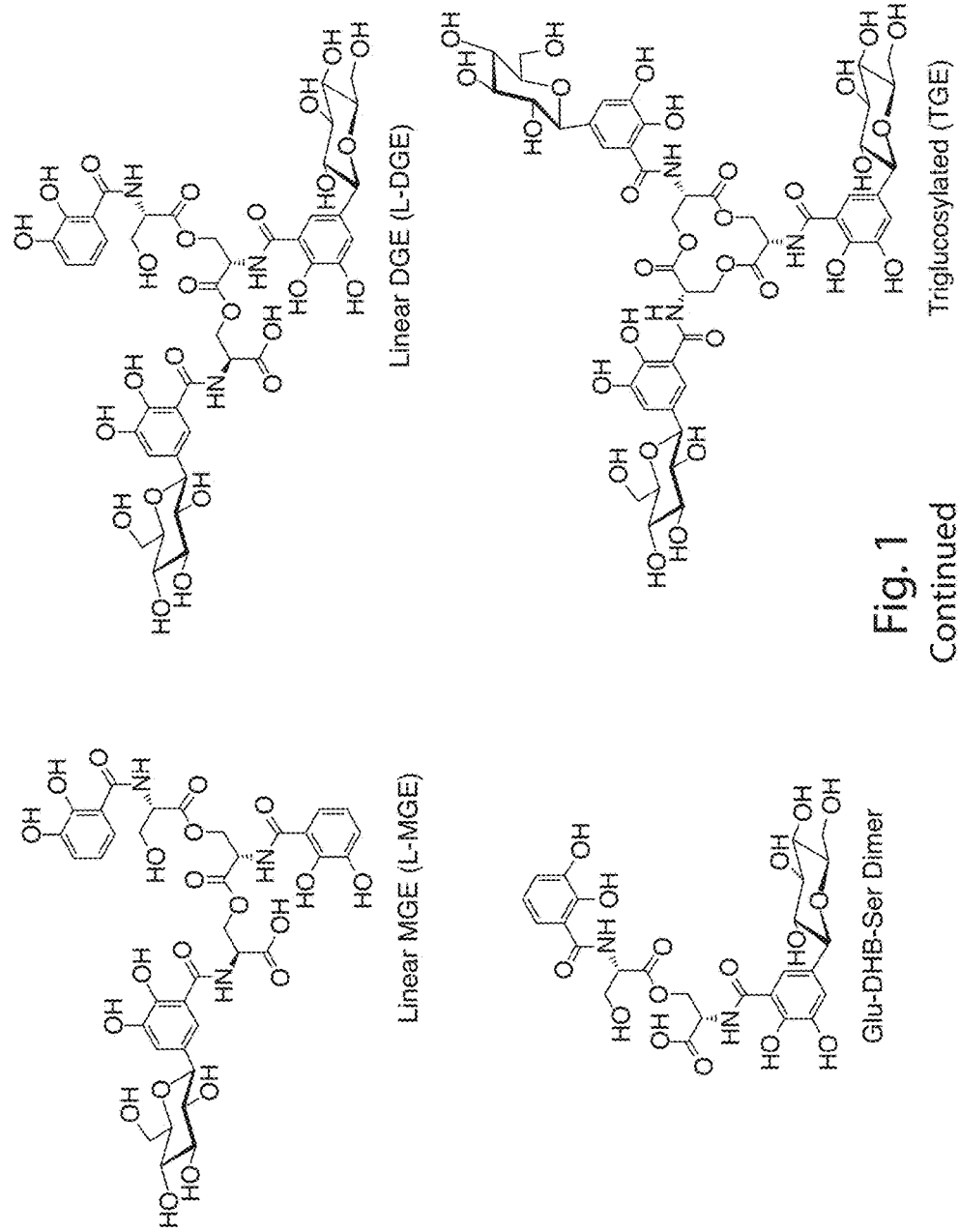
Figure 2:
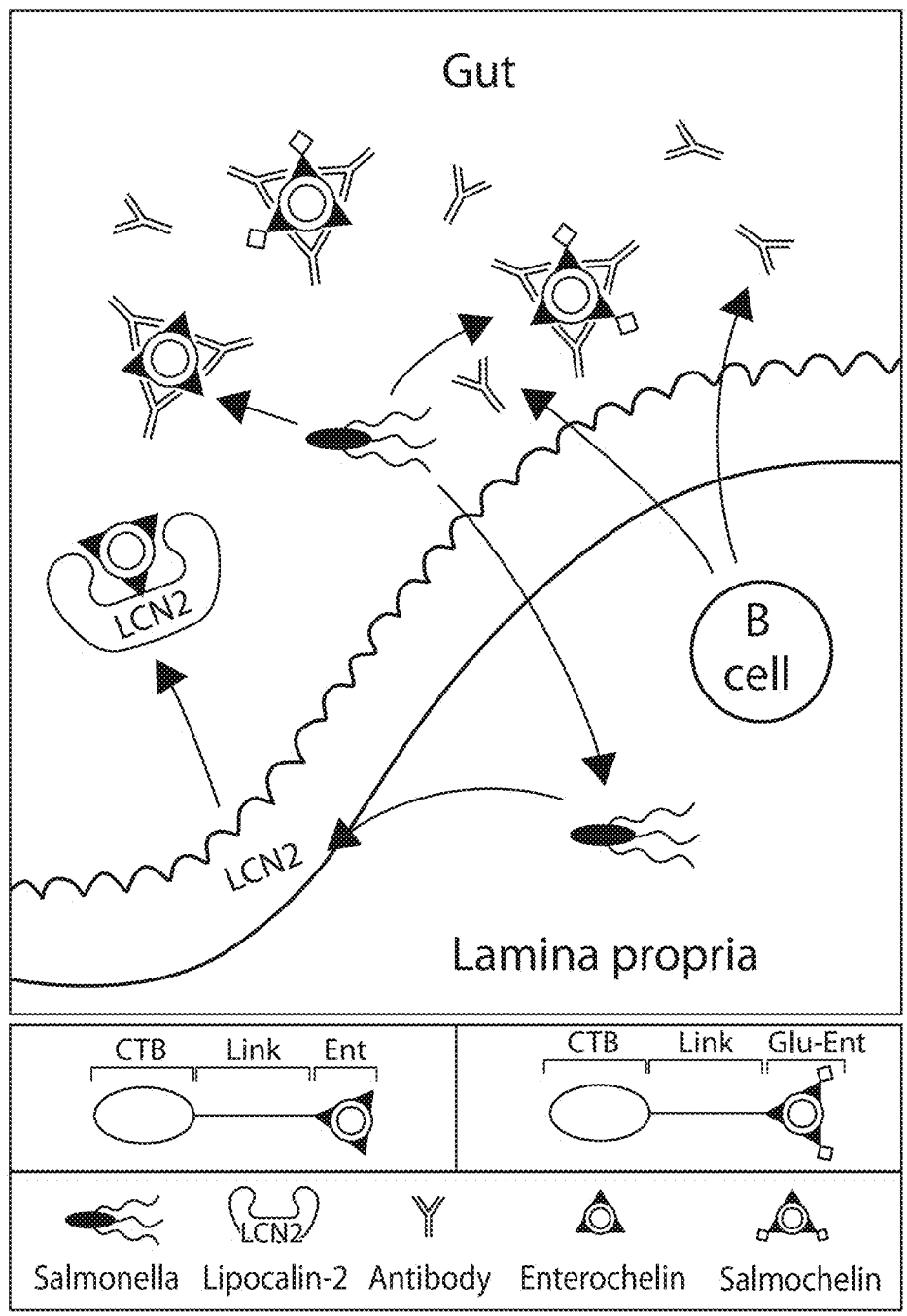
FIG. 2 shows an overview of immunization strategy described for *Salmonella*. Following vaccination with CTB-Ent or another conjugate, antibodies against Ent and Glu-Ent (salmochelins) will be produced. These antibodies will capture the catecholate siderophores Ent and Glu-Ent produced by *Salmonella* and thereby block acquisition of the essential nutrient iron by these pathogens. This strategy is expected to be effective against other species of Enterobacteriaceae such as *Escherichia coli* that utilize Ent and Glu-Ent for iron acquisition.

Salmochelins are a family of glucosylated enterobactin derivatives where the sugar moieties are attached to the C5 position of one or more catecholate rings (e.g., compounds MGE and DGE in FIG. 1). Many pathogenic strains have the capacity to biosynthesize salmochelins, C-glucosylated analogs of enterobactin. Many biological and animal studies have demonstrated that salmochelin biosynthesis and acquisition are essential for the establishment of infection in mouse models of infection. Thus, the ability to induce an immune response including antibodies that selectively bind to salmochelin, or to produce antibodies that selectively bind to salmochelin, may be useful to treatment or prevention or human disease and bacterial pathogenesis.

Salmochelins are produced by species that harbor the iroA gene cluster (iroBCDEN). This gene cluster contains genes encoding enterobactin modification enzymes (IroBDE) and transport machinery (IroCN). IroB is a C-glucosyltransferase that attaches a glucose moiety to one or more of the enterobactin catechol rings via a C-glucosidic bond to afford salmochelins. IroB is expressed by *Salmonella* spp. and certain pathogenic *E. coli* strains, such as *E. coli* CFT073. IroN is the outer membrane receptor for the salmochelins. Similar to FepA, IroN allows the transport of ferric salmochelins (and also ferric enterobactin) into the bacterial cell.

The salmochelins are virulence factors. In addition to providing the pathogens with additional siderophores for iron acquisition, the salmochelins allow pathogens to subvert the host innate immune response. Lipocalin-2 (LCN2) is a host protein that is released by neutrophils and epithelial cells at sites of infection. This protein captures ferric enterobactin with high affinity (e.g., sub-nanomolar or low-nanomolar) and thereby prevents enterobactin-utilizing bacteria from acquiring iron via this siderophore. In contrast, LCN2 cannot capture the salmochelins because the glucose moieties are bulky and prevent LCN2 binding, and also confer increase hydrophilicity to the siderophore scaffold (the LCN2 binding pocket is hydrophobic). Therefore, a salmochelin-carrier protein conjugate may induce an immune response that is targeted to pathogenic bacterium and leave the commensals unaffected. For example, a salmochelin conjugate described herein (e.g., a compound of Formula (I), wherein Ent is a salmochelin, i.e., Glu-Ent) may induce an immune response that selectively inhibits a pathogenic bacterium.

In certain embodiments, the bacterium described herein (e.g., a Gram-negative bacterium) is in vivo. In certain embodiments, the bacterium is in vitro. In certain embodiments, the bacterium is ex vivo.

Another aspect of the present invention relates to methods of inducing an immune response against an enterobactin or salmochelin molecule or analog thereof including administering to a subject an amount of the compound of Formula (I), or a pharmaceutically acceptable salt thereof, or a pharmaceutical composition thereof effective to induce an immune response against the enterobactin or salmochelin molecule in Formula (I) (including analogs thereof as described herein). Methods of administering an immunogen, optionally with an adjuvant, are well known in the art and can be practiced using the compound of Formula (I) to induce an immune response against an enterobactin or salmochelin molecule, or an analog thereof. The immune response in some embodiments includes antibodies that selectively bind to the enterobactin or salmochelin molecule in Formula (I), or an analog thereof. The antibodies can be IgG, IgM, IgA, IgD or IgE, and in some embodiments are IgG and/or IgA. Adjuvants that can be used include: alum; MF59; R848; cholera toxin; squalene; phosphate adjuvants; tetrachlorodecaoxide; monophosphoryl lipid A (MPL, SmithKline Beecham); saponins including QS21 (SmithKline Beecham); immunostimulatory oligonucleotides (e.g., CpG immunostimulatory oligonucleotides first described by Kreig et al., Nature 374:546-9, 1995); incomplete Freund's adjuvant; complete Freund's adjuvant; montanide; vitamin E and various water-in-oil emulsions prepared from biodegradable oils such as squalene and/or tocopherol; Quil A; Ribi Detox; CRL-1005; or L-121.

Inducing an immune response can include vaccination with the compound of Formula (I) to induce an immune response before infection with a bacteria that produces an enterobactin or salmochelin molecule as contained the compound of formula (I), and thus to provide protective immunity against such bacteria.

The subject in whom an immune response is induced can be one who is infected with, suspected of being infected with, or at risk of being infected with a bacteria that produces an enterobactin or salmochelin molecule, or an analog thereof, as contained the compound of Formula (I).

In another aspect, the present invention provides methods of treating a bacterial infection or inflammatory bowel disease (IBD) in a subject in need thereof using a compound of Formula (I) (e.g., an enterobactin-carrier protein conjugate of Formula (I)), or a pharmaceutical composition thereof. In certain embodiments, the methods of the invention include administering to a subject in need thereof an effective amount of a compound of Formula (I), or a pharmaceutically acceptable salt, hydrate, solvate, polymorph, co-crystal, tautomer, stereoisomer, or isotopically labeled derivative thereof, or a pharmaceutical composition thereof.

In certain embodiments, the present invention provides methods of treating a bacterial infection in a subject thereof. In certain embodiments, the bacterial infection is treated by the methods. In certain embodiments, the bacterial infection is a bacterial infection described herein. In certain embodiments, the bacterial infection is caused by a Gram-negative bacterium (e.g., a Gram-negative bacterium described herein). In certain embodiments, the bacterial infection is a urinary tract infection or a respiratory tract infection (e.g., lung infection), such as an infection by an *E. coli* or *Klebsiella* species.

In certain embodiments, the present invention provides methods of treating inflammatory bowel disease (IBD) in a subject thereof. In certain embodiments, the IBD is treated by the methods.

In certain embodiments, the subject described herein is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In another aspect, the present invention provides methods of preventing a bacterial infection and/or IBD in a subject in need thereof using a compound of Formula (I), or a pharmaceutical composition thereof. In certain embodiments, the methods of the invention include administering to a subject in need thereof an effective amount of a compound of Formula (I), or a pharmaceutically acceptable salt, hydrate, solvate, polymorph, co-crystal, tautomer, stereoisomer, or isotopically labeled derivative thereof, or a pharmaceutical composition thereof, which induces in the subject an immune response, e.g., an antibody response, to the enterobactin or salmochelin. In certain embodiments, the methods of the invention include administering to a subject in need thereof an effective amount of a compound of Formula (I), or a pharmaceutically acceptable salt thereof, or a pharmaceutical composition thereof. In certain embodiments, the methods of the invention include administering to a subject in need thereof a prophylactically effective amount of a compound of Formula (I), or a pharmaceutical composition thereof. In certain embodiments, the bacterial infection and/or IBD is prevented by the methods.

Some fungi have been reported to have the ability to take up enterobactin. Thus, similar methods (and compositions, kits etc.) as described herein for treating bacterial infections are also provided for treating fungal infections.

In still another aspect, the present invention provides the compounds of Formula (I), and pharmaceutically acceptable salts thereof, and pharmaceutical compositions thereof, for use in the treatment of a bacterial infection in a subject in need thereof.

In still another aspect, the present invention provides the compounds of Formula (I), and pharmaceutically acceptable salts thereof, and pharmaceutical compositions thereof, for use in the treatment of IBD in a subject in need thereof.

In still another aspect, the present invention provides the compounds of Formula (I), and pharmaceutically acceptable salts thereof, and pharmaceutically acceptable salt thereof, and pharmaceutical compositions thereof, for use in the prevention of a bacterial infection and/or IBD in a subject in need thereof.

In still another aspect, the present invention provides the compounds of Formula (I), and pharmaceutically acceptable salts thereof, and pharmaceutical compositions thereof, for use in inhibiting the growth of a bacterium.

In yet another aspect, the present invention provides the compounds of Formula (I), and pharmaceutically acceptable salts thereof, and pharmaceutical compositions thereof, for use in killing a bacterium.

In another aspect, methods for producing antibodies that selectively bind an enterobactin or salmochelin molecule, or an analog thereof, are provided. In such methods, an amount of the compound of Formula (I) or the composition thereof that is effective to induce an immune response against the an enterobactin or salmochelin molecule (or analog thereof) in Formula (I) is administered to a subject. The antibodies can then be isolated for the subject, such as for use in the methods described herein. Isolation of the antibodies can be performed by any of the standard methods known in the art, including immunochromatography, Protein A binding, Protein G binding, etc.

Nucleic acid molecules that encode the antibodies can also be isolated and cloned for production of antibodies. For example, the nucleic acid molecules that encode the antibodies can be recombinantly expressed in cells, plants or animals according to standard procedures to produce the antibodies. Likewise, cells that produce the antibodies can be isolated for production of antibodies.

Novel analytical methods also are provided, including enzyme-linked immunosorbent assays (ELISA) and enzyme-linked immunosorbent spot (ELISPOT) assays. In some embodiments, methods for detecting or quantifying antibodies that selectively bind enterobactin and salmochelin, or an analog thereof, are provide that include binding enterobactin or salmochelin (or an analog thereof) to a substrate, optionally wherein the substrate is the interior of a well of a multi-well plate, contacting the substrate with a biological sample from an animal administered with an amount of the compound of Formula (I) or a composition thereof, and detecting or quantifying antibodies in the biological sample that bind to the enterobactin or salmochelin, or an analog thereof, bound to the substrate.

Other methods for detecting or quantifying antibodies that selectively bind enterobactin and salmochelin include binding an antibody that selectively binds enterobactin or salmochelin, or an analog thereof, to a substrate, optionally wherein the substrate is the interior of a well of a multi-well plate, binding enterobactin or salmochelin (or an analog thereof) to the antibody that selectively binds enterobactin or salmochelin, or an analog thereof, to form an antibody-enterobactin complex or a antibody-salmochelin complex (or complex of an enterobactin or salmochelin analog with antibody), contacting the antibody-enterobactin complex or antibody-salmochelin complex with a biological sample from an animal administered with an amount of the compound of Formula (I) or a composition thereof, and detecting or quantifying antibodies in the biological sample that bind to the antibody-enterobactin complex or a antibody-salmochelin complex.

Methods also are provided for detecting or quantifying cells that produce antibodies that selectively bind enterobactin and salmochelin. The methods include binding enterobactin or salmochelin, or an analog thereof, to a substrate, optionally wherein the substrate is the interior of a well of a multi-well plate, contacting the substrate with a biological sample containing B cells from an animal administered with an amount of the compound of Formula (I) or a composition thereof, and detecting or quantifying antibodies, secreted by the B cells after contact with the enterobactin or the salmochelin, or an analog thereof, that bind to the enterobactin or salmochelin, or an analog thereof, bound to the substrate.

In some embodiments the antibodies that bind to the enterobactin or salmochelin, or an analog thereof, or to the antibody-enterobactin complex or antibody-salmochelin complex (or corresponding complex with an analog thereof) are detected or quantified by binding with an enzyme-linked antibody that binds to antibodies of the animal, such as goat-anti-mouse antibodies for antibodies from a mouse (i.e., from a mouse biological sample) or rabbit-anti-human antibodies for antibodies from a human (i.e., from a human biological sample). The enzyme-linked antibody then is incubated with a substrate for the enzyme that produces a detectable molecule when acted upon by the enzyme, such as colored product, a fluorescent product, a chemiluminescent product, or a PCR product. Typical enzymes used in such procedures include horseradish peroxidase and alkaline phosphatase. The detectable product then is detected or quantified, which correlates to detecting or quantifying the antibodies in the biological sample.

The ability to produce antibodies that selectively bind enterobactin and salmochelin using the compound of Formula (I) facilitates methods for producing fecal microbiota transplant (FMT) material. FMT is becoming often a treatment for recurrent infections with *Clostridium difficile*, and it has been proposed also for other diseases characterized by intestinal inflammation. The fecal material to be transferred comes from a healthy donor chosen by the patient; however, at present the microbiota of the donor is not analyzed. A potential issue is that the microbiota that gets administered to patients may contain pathobionts (e.g. a commensal strain with potential to cause disease) like *E. coli* LF82, which may trigger inflammatory bowel disease in predispose individuals. In some aspects, fecal material to be used as transplant material is contacted with antibodies that selectively bind enterobactin and salmochelin. In other aspects, the antibodies that selectively bind enterobactin or salmochelin are administered with the FMT material. By administering our antibodies with the fecal material, the growth of potentially dangerous species of bacteria in the FMT material is reduced.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Immunogenic Protein-Siderophore Conjugates

FIG. 3 provides a generalized depiction for immunogenic protein-siderophore conjugates in which an immunogenic carrier protein (CP) is attached to Ent or Glu-Ent (a monoglucosylated form is shown in FIG. 3B) via a stable polyethylene glycol ($PEG_3$) linker. The CP may be one of several carrier proteins—Cholera toxin B subunit (CTB), keyhole limpet hemocyanin (KLH), ovalbumin (OVA), etc. (see, e.g., Bioinformatics (2006) 22 (2): 253-255). Moreover, the method of attachment of the siderophore to the carrier protein can be varied. The strategies shown in FIGS. 3 and 4 are based on a peptide coupling strategy where free lysine residues on the surface of the carrier protein are coupled to a free carboxylic acid (activated as a NHS ester) of the $PEG_3$ linker. (Ent derivatized with a carboxylic acid in the $C_5$ position could also be attached directly to surface Lys residues of a carrier protein.) FIG. 4 summarizes the optimized synthesis/preparation of CTB-Ent. The $PEG_3$ linker is important because it provides spatial separation (~14 Å) between CTB and the Ent moiety. Characterization of CTB-Ent by SDS-PAGE, HPLC, and optical absorption spectroscopy revealed successful conjugation and an Ent/CTB ratio of ca. 4:1, the latter of which indicates that ~45% of the CTB Lys residues were Ent-modified. This preparative route is now optimized and highly reproducible, with each synthesis affording multi-milligram quantities of CTB-Ent. Thus, from one synthetic batch of CTB-Ent prepared on a 4-mg scale, 20 animals (mice) can be immunized for our studies. Alternative preparative routes are required to prepare Glu-Ent conjugates (FIG. 3B) and some examples of possible alternative routes are given in FIG. 5, FIG. 15B and FIG. 15C.

Example 2

Mucosal Immunization with CTB/CTB-Ent Conjugates 6-8 weeks old $C_{57}BL/6$ mice were immunized intranasally with either 100 μg of CTB-Ent or CTB (Sigma). Mice were also boosted 14 days later with 100 μg of either CTB or CTB-Ent. To monitor the health of the animals during the immunization period, mice were weighed every week.

Fecal Pellet Extracts for Antibody Detection Fresh fecal samples were collected every week during the immunization period. Fecal pellets were resuspendend in 400 μL of sterile PBS containing a protease inhibitor cocktail (Roche Mini EDTA-Free, EASYpack) and were shaken at RT for 30 minutes. Samples were spun down at 7200 g for 20 minutes at room temperature and the supernatants were collected individually and stored at −20° C. until further analysis.

ELISA for IgA Detection

In order to measure anti-enterobactin (Ent) and anti-salmochelin (Glu-Ent) IgA antibodies by ELISA, 96-well plates (NUNC MAXIsorp) were incubated overnight at 4° C. or 2 h at 37° C. with 1 g/mL of biotinylated Ent or Glu-Ent diluted in sterile PBS pH 7.4. The plates were then blocked for 1 h at 37° C. with 5% non-fat milk. Serial dilutions of fecal extracts from CTB immunized (mock) and CTB-Ent immunized mice were added to the wells, starting from 1:10 dilution. The presence of specific IgA was evaluated by adding a goat anti-mouse IgA conjugated with horseradish peroxidase (1:5000; Southern Biotechnology Associates, Inc., Birmingham, Ala., USA) and incubated for 1 h at 37° C. This procedure was followed by detection with horseradish peroxidase substrate where O-phenyl legediamine tablets (Sigma) were dissolved in 1× phosphate-citrate buffer and 60 μL of hydrogen peroxide (Sigma) were added. The reaction was blocked with 2 N hydrogen sulfate.

Figure 6:
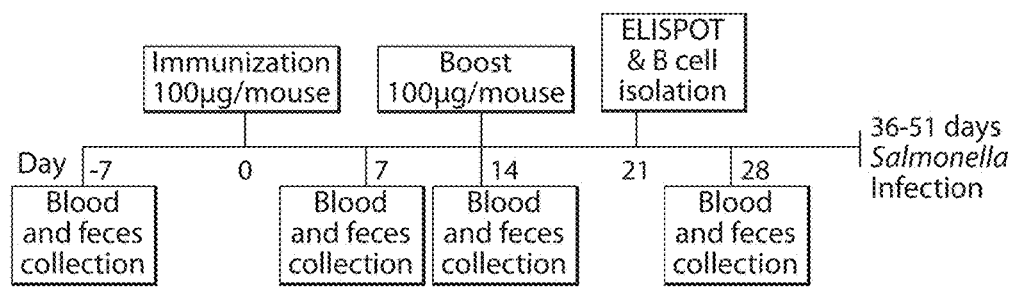
FIG. 6 shows an immunization protocol used. Shown are the timing and dose of immunization; the timing of feces and blood collection; and the day in which the cells were isolated for the ELISPOT assay.
Figure 7D:
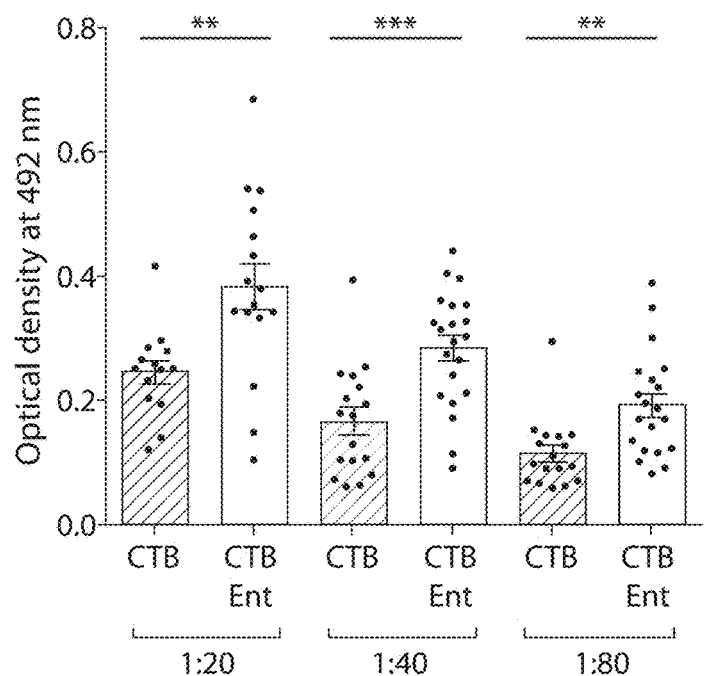

Pilot studies were performed to determine whether CTB-Ent induces an antibody response in mice and to determine whether antibodies specific to Ent and/or Glu-Ent are formed. FIG. 6 summarizes the protocol employed for these studies. $C_{57}BL/6$ mice were immunized intranasally with either 100 pg of CTB-Ent (n=20) or CTB (n=24) (first immunization and boost 14 days later). The two immunizations were well tolerated; the mice did not develop any sign of disease when monitored for up to 51 days after the first immunization. To determine whether antibodies binding Ent and Glu-Ent were produced in immunized mice, blood and fecal samples were collected weekly and an in-house ELISA was developed to detect antibodies against Ent/Glu-Ent. The results from ELISA are presented in FIGS. 7A-7D show that the presence of specific anti-Ent IgA antibodies was detected in the feces from CTB-Ent immunized mice at 14-21 days post-immunization that persisted up to 51 days post-immunization (n=5-10) (FIGS. 7A, 7C and 7B). Furthermore, IgA antibodies were also detected from fecal extracts that cross-react with Glu-Ent, as predicted because of their structure similarities (FIGS. 7B and 7D). These results show that IgA binding to Glu-Ent (di-glucosylated form) was detected in fecal samples of mice immunized with CTB-Ent at day 21 post-immunization.

Example 3

ELISPOT for Detection of IgA-Producing B Cells

A multi-screen ELISPOT PVDF (Millipore) membrane plate was washed with 35% ethanol and then was coated with 1 μg/mL of the antigen (Ent or Glu-Ent) diluted in sterile PBS and incubated at 4° C. overnight. The plate was then blocked for 1 h at RT shaking by the addition of RPMI+10% FBS. Cells isolated from the intestinal mucosa (i.e. Peyer's patches, mesenteric lymph nodes) and, as a control, a non-mucosal site (i.e. spleen) from CTB immunized (mock) and CTB-Ent immunized mice were resuspended in RPMI+10% FBS and seeded at a density of $2.5\times10^5$ cells/well or lower in duplicates. Then, the plate was incubated at 37° C. 5% $CO_2$ for at least 18 h. The cells were washed out and specific antibodies were detected after incubation for 2 h at RT shaking with goat anti-mouse IgA secondary antibody at 0.5 g/ml (Southern Biotechnology Associates, Inc., Birmingham, Ala., USA), and addition of 3-amino-9-ethylcarbazole (AEC), then visualized, and counted with the CTL Immunospot software (Cellular Technology Limited).

Bacterial Strains and Growth Conditions

IR715 is a fully virulent, nalidixic acid-resistant derivative of Salmonella enterica serovar Typhimurium wild-type isolate ATCC14028. The strain was routinely grown aerobically in Luria-Bertani broth (10 g/L tryptone, 5 g/L yeast extract, 10 g/L NaCl) or in LB agar plates at 37° C.

To further confirm the production of antibodies, ELISPOT assays were designed and performed, which allow for the detection of single antibody-secreting cells. Briefly, a multi-screen ELISPOT PVDF membrane plate was coated with Ent or Glu-Ent. Cells isolated from the Peyer's patches at day 21 post-immunization were resuspended in culture media and seeded at a density of $2.5\times10^5$ cells/well or lower. Then, the plate was incubated at 37° C. 5% $CO_2$ overnight. After being restimulated by the contact with the Ent antigen, specific antibody-producing B cells secreted antibodies that formed an immune complex with the immobilized Ent antigen or Glu-Ent antigen. The immunocomplexes were detected after incubation with HRP-conjugated anti-IgA, and addition of the 3-amino-9-ethylcarbazole, (AEC) then visualized and counted with the CTL Immunospot software (Cellular Technology Limited). FIGS. 8A-8D show that we detected "spots" representing Ent-antibody complexes or Glu-Ent-antibody complexes only in mice immunized with CTB-Ent but not in mock-immunized mice.

Example 4

Salmonella Typhimurium Acute Model of Gastrointestinal Infection

Between 36-51 days post-immunization, $C_{57}BL/6$ immunized mice were treated with streptomycin (100 μL of a 200 mg/mL solution in sterile water) one day prior to infection. The following day the mice were orally inoculated with $10^9$ CFU of S. Typhimurium (resuspended in 0.1 mL of LB broth). Fecal material was collected each day after bacterial administration, harvested in sterile PBS, and the bacterial load was determined by plating serial 10-fold dilutions on selective agar plates. Between 4-6 days post infection, mice were euthanized and cecum was collected for isolation of mRNA and protein and for histopathological analysis, flash frozen and stored at −80° C. Bacteria were enumerated in the colon content, terminal ileum, Peyer's Patches, and S. Typhimurium dissemination in the spleen by plating serial dilutions on LB agar plates containing the appropriate antibiotics.

Statistical Analysis

Statistical analysis was performed by using Graphpad Prism 6. The Mann-Whitney non-paired test was used.

Studies also were performed to determine whether this mucosal immunization provides protection against Salmonella challenge in immunized mice. Briefly, groups of 5-10 CTB-siderophore immunized and CTB-immunized (mock) mice were treated with streptomycin (to induce a proinflammatory response and neutrophil influx in the cecum) one day before infection with $1\times10^9$ CFU of wild-type serotype Typhimurium 14028 (O antigen group B). The resulting data are presented in FIGS. 9-12. Consistent with prior studies, S. Typhimurium intestinal colonization reached its peak at 4 days after infection in CTB (mock)-immunized mice, which had to be euthanized because of a ~10% weight loss. In marked contrast, mice that were immunized with CTB-Ent showed a significantly lower weight loss (~6%, P=0.05; FIG. 12A) and lower bacterial burden of S. Typhimurium in the colon content at 96 h after infection (P=0.0001) (FIG. 9). It should be noted that S. Typhimurium colonization was not lower in the colon content of all CTB-Ent-immunized mice. Nonetheless, the levels of S. Typhimurium colonization in the colon content correlated with the levels of Ent-specific IgA detected by ELISA ($R^2$=0.53; P=0.0002) (FIG. 10). Moreover, the "responders" or mice that showed both a mucosal antibody response and lower Salmonella burden also showed a lower Salmonella burden at 96 h after infection (terminal ileum, FIG. 11A; Peyer's patches, FIG. 1B; spleen, FIG. 12B). These results indicate that the success of immunization in terms of response to the infectious challenge may be predicted by measuring the fecal antibody response to Ent. Hence, future identification of low/non responders by a simple analysis of the antibodies in the feces may lead to improved strategies to ameliorate their response (for instance, the addition of a third boost, the increase of the dose of antigens, and the administration of an adjuvant).

Example 5

Quantitative Real-time PCR

For analysis of gene expression by quantitative real-time PCR, total RNA was extracted from cecal and hepatic tissues with TRI Reagent (Molecular Research Center; Cincinnati, Ohio). Real-time PCR was performed using SYBR Green (Roche, Indianapolis, Ind.) and the Roche Lightcycler 480 system (Roche, Indianapolis, Ind.). The data were analyzed using the comparative ΔΔ-Ct method. Target gene transcription of each sample was normalized to the respective levels of ActB (encoding for β-actin) mRNA. Uninfected, streptomycin-treated mice were used as controls.

Histopathology Analysis

Tissue samples were fixed in formalin, processed according to standard procedures for paraffin embedding, sectioned at 5 µm, and stained with hematoxylin and eosin. The pathology score of cecal samples was determined by blinded examinations of cecal sections from a board-certified pathologist using previously published methods (Barthel et al., *Infection and Immunity* 2003, 71(5), p 2839-2858; Raffatellu et al., *Cell Host and Microbe* 2009, 5(5), p. 476-486). Each section was evaluated for the presence of neutrophils, mononuclear infiltrate, submucosal edema, surface erosions, inflammatory exudates, and cryptitis. Inflammatory changes were scored from 0 to 4 according to the following scale: 0=none; 1=low; 2=moderate; 3=high; 4=extreme. The inflammation score was calculated by adding up all the scores obtained for each parameter and interpreted as follows: 0-2=within normal limit; 3-5=mild; 6-8=moderate; 8+=severe.

In another set of experiments, the effect of CTB-Ent immunization on the global immune response to *Salmonella* infection was evaluated. The data set is provided in FIG. 13A (and data not shown). The data indicates that pro-inflammatory cytokines (IL-17, IL-22), as well as Lcn2, are similarly upregulated in response to infection in both CTB-immunized and CTB-Ent immunized mice as compared to uninfected mice.

Histopathology analysis is shown in FIG. 13B, for both CTB-immunized (day 4 post-infection) and CTB-Ent immunized mice (days 4 and 6 post-infection).

Example 6

Microbiota Analysis

DNA from the colon content was extracted with the QIAamp DNA stool kit (QIAGEN). Bacterial DNA was amplified by a two-step PCR enrichment of the 16S rDNA (V4 region) encoding sequences from each sample with primers 515F and 806R modified by addition of barcodes for multiplexing. Libraries were sequenced using an Illumina MiSeq system at the UC Davis Host Microbe Systems Biology Core. Uncalled bases, incorrect primer sequence, and runs of ≥12 identical nucleotides sequences were removed. Following quality filtering, the sequences were demultiplexed and trimmed before performing sequence alignments, identification of operational taxonomic units (OTU), clustering, and phylogenetic analysis using QIIME open-source software.

The microbiota were analyzed in mice either mock immunized (CTB, n=8) or immunized with CTB-Ent (n=8). Of each group, 3 mice were mock-infected, while 5 were infected with *S. Typhimurium* for 4 days. The results (FIGS. 14A-14C) suggest that immunization with either CTB or CTB-Ent did not alter the composition of the microbiota. Furthermore, *S. Typhimurium* constituted the largest fraction (ca. 32%) of the intestinal microbes in infected mice immunized with CTB, which is consistent with an earlier study from naive mice. In contrast, *S. Typhimurium* dropped to a mere 7% in mice immunized with CTB-Ent, which is consistent with the observed reduction in CFUs (see FIG. 9). Even more remarkable, the reduction of *Salmonella* colonization was accompanied by an expansion of *Lactobacillus* spp. (from ~19% in CTB immunized, infected to ~60% in CTB-Ent immunized, infected), beneficial microbes that are likely able to thrive in the inflamed gut also because of their minimal requirement for Fe. Altogether, these promising results suggest that siderophore immunization per se does not alter the intestinal microbiota. Moreover, the reduction of *Salmonella* intestinal colonization may allow for the growth of beneficial microbes like *Lactobacillus* spp in the inflamed gut. This overall outcome would be beneficial for the host. These data also show a reduction in other enteric bacteria and suggest that this mucosal immunization strategy may be of benefit for inflammatory bowel disease or other conditions in which the intestine is inflamed and Enterobacteriaceae predominate. Of note, a low level of *Escherichia* spp. was detected in mock-immunized mice, which was further reduced in CTB-Ent immunized mice.

Example 7

CTB-Ent Synthesis 1-(3,4-Bis(benzyloxy)-5-(((3S,7S,11S)-7,11-bis(2,3-bis(benzyloxy)benzamido)-2,6,10-trioxo-1,5,9-trioxacyclododecan-3-yl)carbamoyl)phenyl)-1-oxo-5,8,11-trioxa-2-azatetradecan-14-oic acid (4)

To a 10-mL round-bottom flask, $PEG_3$.TFA 2 (38.9 mg, 116 µmol) was dissolved in 500 µL of anhydrous DMSO. Trimethylsilyl chloride ($TMSC_1$, 15.6 µL, 123 µmol) and N,N-diisopropylethylamine (DIPEA, 21.4 µL, 123 µmol) were then added. The mixture was purged with $N_2$ three times and stirred at room temperature for 10 min. To another 10-mL round-bottom flask, enterobactin acid 3 (96.3 mg, 76.8 µmol), HATU (32.1 mg, 84.5 µmol), and HOAT (11.5 mg, 84.5 µmol) were dissolved in 1 mL of anhydrous DMSO and the mixture was purged with $N_2$ three times. DIPEA (53.5 µL, 307.2 µmol) was then added and the reaction was stirred at room temperature for 5 min. The resulting bright yellow solution was then transferred to a solution of in situ protected $PEG_3$ amine. The reaction was stirred at room temperature. After 2 h, the reaction was partitioned in water (20 mL) and EtOAc (20 mL). The organic layer was washed with 0.1 M HCl (3×10 mL) and brine (1×10 mL), and dried over anhydrous $Na_2SO_4$. The solvents were removed by rotary evaporation. The crude product was purified by preparative TLC (100% EtOAc, and then the plate was dried and then run a second time in 7% $MeOH/CH_2Cl_2$) to yield 4 as a white solid (67.7 mg, 61%). $R_f$=0.5 (10% MeOH/$CH_2Cl_2$). $^1H$ NMR (500 MHz, $CDCl_3$) δ 2.59 (t, J=6.0 Hz, 2H), 3.58-3.72 (m, 12H), 3.77 (t, J=6.5 Hz, 2H), 3.97-4.07 (m, 3H), 4.08-4.17 (m, 3H), 4.85-4.94 (m, 3H), 5.01-5.22 (m, 12H), 7.06-7.46 (m, 31H), 7.65 (dd, J=6.8, 2 Hz, 2H), 7.79 (br, 1H), 7.90 (d, J=1.6 Hz, 1H), 8.16 (d, J=1.6 Hz, 1H), 8.49 (d, J=6.8 Hz, 2H), 8.66 (d, J=6.8 Hz, 1H). $^{13}C$ NMR (125 MHz, CDCl3) δ 30.0, 40.0, 51.4, 63.8, 66.7, 69.7, 69.9, 70.2, 71.2, 76.3, 117.5, 121.0, 123.0, 124.3, 126.2, 127.6, 127.7, 128.0, 128.2, 128.4, 128.5, 128.5, 128.6, 128.8, 128.9, 128.9, 129.0, 135.4, 135.9, 136.0, 136.2, 146.8, 146.9, 149.0, 151.6, 165.0, 168.9, 169.1. HRMS (ESI): $[M+Na]^+$ m/z calcd, 1479.5213. found, 1479.5500.

1-(3-(((3S,7S,11S)-7,11-Bis(2,3-dihydroxybenzamido)-2,6,10-trioxo-1,5,9-trioxacyclo dodecan-3-yl)carbamoyl)-4,5-dihydroxyphenyl)-1-oxo-5,8,11-trioxa-2-azatetradecan-14-oic acid (5)

$Bn_6Ent-PEG_3$ acid 4 (49.6 mg, 34.1 µmol) was dissolved in 4 mL of 1:1 EtOH/EtOAc and 50 mg of Pd/C (10% wt, Sigma-Aldrich) was added after the flask was purged with N$_2$ three times. The reaction was stirred under H$_2$ (1 atm) for 6 h at room temperature. Pd/C was removed by centrifuging at 13,000 rpm for 10 min. The supernatant was collected and concentrated by rotary evaporation to afford an off-white residue. The crude product was dissolved in 2:2:1 H$_2$O/MeCN/DMSO and purified by semi-preparative HPLC (25-34% B over 15 min, 4 mL/min). The product eluted at 11.8 min and was lyophilized to yield Ent-PEG$_3$ acid 5 as a white powder (24.6 mg, 78%). HPLC retention time=17.3 min (0-100% B over 30 min, 1 mL/min where solvent B is MeCN with 0.1% TFA). The analytical HPLC trace is shown in FIG. 17. $^1$H NMR (500 MHz, CD$_3$OD) δ 2.49 (t, J=6.2 Hz, 2H), 3.50-3.56 (m, 4H), 3.57-3.64 (m, 8H), 3.66 (t, J=6.3 Hz, 2H), 6.70 (t, J=8.0 Hz, 2H), 6.94 (ddd, J=7.9, 2.4, 1.6 Hz, 2H), 7.23 (ddd, J=8.2, 5.3, 1.6 Hz, 2H), 7.44 (d, J=2.2 Hz, 1H), 7.86 (d, J=2.2 Hz, 1H). $^{13}$C NMR (125 MHz, MeOD) δ 35.7, 41.0, 53.6, 65.8, 67.8, 70.5, 71.2, 71.3, 71.4, 71.5, 116.6, 116.7, 118.6, 119.5, 119.7, 120.1, 126.5, 143.1, 147.2, 149.4, 152.2, 169.3, 170.0, 175.4. HRMS (ESI): [M+Na]+m/z calcd, 939.2396. found, 939.2395.

Conjugation of Ent-PEG$_3$ Acid 5 to Chlorea Toxin Subunit B (CTB) Stock solutions of EDC (100 g/μL) and NHS (60 g/μL) were prepared in anhydrous DMSO. A 5-μL aliquot of the EDC solution was added to Ent-PEG$_3$ acid 5 (800 μg, 873 nmol) followed by the addition of a 5-μL aliquot of the NHS solution. The progress of the reaction was monitored by analytical HPLC, and the reaction was complete after 2 h. Fe(acac)$_3$ (293 μg, 830 nmol) in DMSO was then added to Ent-PEG$_3$-NHS 6 before the coupling step to afford the iron-bound form. Without any further purification, complex 7 was added to a 100-μL solution of CTB (200 μg, 17.2 nmol, Sigma-Aldrich) in 100 mM sodium phosphate, pH 8. The reaction was incubated for 3 h at room temperature. Following incubation, the reaction was subjected to eight rounds of spin-filtration (MWCO=3 kDa, EMD Millipore) at 13,000 rpm for 15 min with PBS, pH 7.2 to remove any unreacted 7 and coupling reagents. The solution of CTB-Ent 8 was stored in PBS at 4° C. until being used for immunization.

Synthesis of CTB-Ent Conjugate

To obtain CTB-Ent conjugate 8, carboxyl and amine cross-linking was employed using 1-ethyl-3-(3-dimethylaminopropyl)carbodiimide (EDC) and N-hydroxysuccinimide (NHS) as coupling reagents. We modified Ent acid 3 (see FIG. 16) with a polyethylene glycol (PEG) linker housing a terminal carboxylic acid for coupling to the free lysine residues on CTB. Because the Ent moiety decomposes in the presence of acids, including trifluoroacetic acid (TFA), the PEG$_3$ ester 1 was hydrolyzed to yield PEG$_3$ 2 prior to coupling to 3. The benzyl-protected Ent-$PEG_3$ acid 4 as a white solid in 61% yield after purification by preparative TLC. Deprotection of the benzyl groups was performed by hydrogenation (1 atm) over Pd/C. This reaction was complete after 6 h. The crude product was purified by semi-preparative HPLC to yield Ent-$PEG_3$ acid 5 as a white powder in milligram quantities and in high purity. The purity and identity of 5 were confirmed by using analytical HPLC, LC/MS, $^1$H and $^{13}$C NMR. Subsequently, compound 5 was pre-activated for the next coupling step via NHS ester synthesis. Because the Ent trilactone ring slowly undergoes hydrolysis in aqueous solution, one equivalent of $Fe(acac)_3$ in DMSO was added to Ent-PEG3-NHS 6 before the coupling step to afford the iron-bound form 7, which is less susceptible to hydrolysis under these reaction conditions. The solution immediately turned dark reddish purple as a result of iron chelation, indicating that complex 7 was formed. Without any further purification, 7 was added to a solution of CTB in sodium phosphate pH 8. Following a 3-h incubation at room temperature, the reaction was subjected to extensive spin-filtration (MWCO=3 kDa) with phosphate buffer saline (PBS) pH 7.2 to remove any unreacted 7 and coupling reagents. The flow through was light purple, and the retentate remained dark purple after the eighth spin-filtration, indicating that iron-bound Ent was successfully attached to CTB. The resulting conjugate 8 was stored in PBS pH 7.2 at 4° C. until being used for immunization.

Characterization of CTB-Ent Conjugate 8

UV-Visible Absorption Spectroscopy

To approximate the ratio of Ent/CTB resulting from the coupling reaction, the UV-visible spectra of CTB-Ent 8 (FIG. 18) were recorded. One CTB subunit contains 9 lysine residues and the calculations by using the absorption at 280 and 495 nm ($\epsilon_{280}$ of CTB=10095 $M^{-1}$ $cm^{-1}$, $\epsilon_{280}$ of $[FeEnt]^{3-}$=8200 $M^{-1}$ $cm^{-1}$, $\epsilon_{495}$ of $[FeEnt]^{3-}$=5500 $M^{-1}$ $cm^{-1}$ in PBS pH 7.2) indicated that the number of Ent molecules per one CTB molecule was approximately 3.5.

SDS-PAGE Analysis

Samples of CTB and CTB-Ent were analyzed by SDS-PAGE using a 16% tricine gel. A 10-μL aliquot of CTB-Ent 8 from each reaction as well as unmodified CTB were diluted with Milli-Q water to 20 μL, and 5 μL of 5×SDS-PAGE gel loading buffer was added to each sample. The samples were boiled for 5 min and analyzed (120 V, 2 h; FIG. 19). The lowest band in lane 2 is higher than the unmodified CTB band in lane 1. This comparison suggests that Ent molecules are attached to CTB. The identity of the band at 25 kDa is unclear; however, it also appeared in lane 4, suggesting that the excess coupling reagents may react with CTB.

Equivalents And Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

CP-(L-Ent)$_n$ (I)

wherein CP is a carrier protein that does not comprise a maleimide moiety, L is a liner, Ent is enterobactin or a salmochelin, n is a number between 1-400, inclusive, and wherein L-Ent is attached to a lysine residue of the carrier protein;
or a salt, hydrate, solvate, polymorph, co-crystal, tautomer, stereoisomer, or isotopically labeled derivative thereof.

2. The compound of claim 1, wherein the carrier proteins is cholera toxin B submit (CTB), keyhole limpet hemocyanin (KLH), ovalbumin (OVA), *Concholepas concholepas* hemocyanin (CCH) or bovine serum albumin (BSA).

3. The compound of claim 1, wherein the linker is a poly(ethylene glycol) (PEG) molecule.

4. The compound of claim 3, wherein the PEG molecule has 1-10 PEG units (PEG$_1$-PEG$_{10}$).

5. The compound of claim 4, wherein the PEG molecule is a PEG$_3$ molecule.

6. The compound of claim 1, wherein at least one L-Ent is attached to each carrier protein (n is greater than 1).

7. The compound of claim 6, wherein n=5-300.

8. The compound of claim 1, wherein the Ent is complexed with iron.

9. A composition comprising the compound of claim 1.

10. The composition of claim 9, further comprising an immunological adjuvant.

11. A method for inducing an immune response against an enterobactin or salmochelin molecule, comprising
administering to a subject an amount of the compound of claim 1 effective to induce an immune response against the enterobactin or salmochelin molecule in formula (I).

12. The method of claim 11 wherein the immune response comprises antibodies that selectively bind to the enterobactin or salmochelin molecule in formula (I).

13. The method of claim 11, wherein the subject is infected with, suspected of being infected with, or at risk of being infected with a bacteria that produces an enterobactin or salmochelin molecule as contained the compound of formula (I).

* * * * *